US008211279B2

(12) United States Patent
Bard et al.

(10) Patent No.: US 8,211,279 B2
(45) Date of Patent: Jul. 3, 2012

(54) ELECTROCHEMISTRY AND ELECTROGENERATED CHEMILUMINESCENCE WITH A SINGLE FARADAIC ELECTRODE

(75) Inventors: Allen J. Bard, Austin, TX (US); Chong-Yang Liu, Austin, TX (US)

(73) Assignee: Board of Regents of the University of Texas System, Austin, TX (US)

( * ) Notice: Subject to any disclaimer, the term of this patent is extended or adjusted under 35 U.S.C. 154(b) by 1122 days.

(21) Appl. No.: 11/446,596

(22) Filed: Jun. 2, 2006

(65) Prior Publication Data

US 2007/0034529 A1 Feb. 15, 2007

Related U.S. Application Data

(60) Provisional application No. 60/686,935, filed on Jun. 3, 2005, provisional application No. 60/695,163, filed on Jun. 30, 2005, provisional application No. 60/737,472, filed on Nov. 17, 2005.

(51) Int. Cl.
*G01N 27/26* (2006.01)
(52) U.S. Cl. .......................................... 204/400; 422/52
(58) Field of Classification Search ............ 422/52, 422/82.07, 82.018; 204/403, 412, 400; 252/700, 252/583, 586, 301.16–301.35; 436/172
See application file for complete search history.

(56) References Cited

U.S. PATENT DOCUMENTS

| 3,319,132 A | 5/1967 | Chandross et al. |
| 3,583,230 A | 6/1971 | Patterson |
| 3,676,784 A | 7/1972 | Le Comte |
| 3,816,795 A | 6/1974 | Maricle et al. |
| 3,900,418 A | 8/1975 | Bard et al. |
| 3,961,253 A | 6/1976 | Brych |
| 3,970,518 A | 7/1976 | Giaever |
| 3,984,688 A | 10/1976 | Von Bargen et al. |
| 4,007,011 A | 2/1977 | Greaves et al. |
| 4,070,246 A | 1/1978 | Kennedy et al. |
| 4,115,535 A | 9/1978 | Giaever |
| 4,132,605 A | 1/1979 | Tench et al. |
| 4,169,804 A | 10/1979 | Yapel, Jr. |
| 4,200,607 A | 4/1980 | Suzuki |
| 4,210,724 A | 7/1980 | Sogi et al. |

(Continued)

FOREIGN PATENT DOCUMENTS

EP 0 180 384 A2 5/1986

(Continued)

OTHER PUBLICATIONS

Japanese Abstract of JP 5-199898 A, "Detection of Gene", Koji et al., Publication Date Aug. 10, 1993.

(Continued)

*Primary Examiner* — Alex Noguerola
*Assistant Examiner* — Gurpreet Kaur
(74) *Attorney, Agent, or Firm* — Foley & Lardner LLP

(57) ABSTRACT

Described herein is an apparatus comprising an electrochemical cell that employs a capacitive counter electrode and a faradaic working electrode. The capacitive counter electrode reduces the amount of redox products generated at the counter electrode while enabling the working electrode to generate redox products. The electrochemical cell is useful for controlling the redox products generated and/or the timing of the redox product generation. The electrochemical cell is useful in assay methods, including those using electrochemiluminescence. The electrochemical cell can be combined with additional hardware to form instrumentation for assay methods.

17 Claims, 6 Drawing Sheets

U.S. PATENT DOCUMENTS

| | | | |
|---|---|---|---|
| 4,213,703 A | 7/1980 | Haunold et al. |
| 4,280,815 A | 7/1981 | Oberhardt et al. |
| 4,293,310 A | 10/1981 | Weber |
| 4,297,105 A | 10/1981 | Dube |
| 4,303,410 A | 12/1981 | Copeland |
| 4,305,925 A | 12/1981 | Kapmeyer et al. |
| 4,328,185 A | 5/1982 | Reasons et al. |
| 4,419,453 A | 12/1983 | Dorman et al. |
| 4,431,919 A | 2/1984 | Köstlin et al. |
| 4,443,713 A | 4/1984 | Layton |
| 4,447,546 A | 5/1984 | Hirschfeld |
| 4,480,042 A | 10/1984 | Craig et al. |
| 4,515,890 A | 5/1985 | Manderino et al. |
| 4,537,861 A | 8/1985 | Elings et al. |
| 4,539,507 A | 9/1985 | VanSlyke et al. |
| 4,554,088 A | 11/1985 | Whitehead et al. |
| 4,619,745 A | 10/1986 | Porta et al. |
| 4,628,037 A | 12/1986 | Chagnon et al. |
| 4,652,333 A | 3/1987 | Carney |
| 4,661,444 A | 4/1987 | Li |
| 4,677,067 A | 6/1987 | Schwartz et al. |
| 4,695,392 A | 9/1987 | Whitehead et al. |
| 4,695,393 A | 9/1987 | Chagnon et al. |
| 4,698,302 A | 10/1987 | Whitehead et al. |
| 4,731,337 A | 3/1988 | Luotola et al. |
| 4,745,076 A | 5/1988 | Müller et al. |
| 4,745,077 A | 5/1988 | Holian et al. |
| 4,771,215 A | 9/1988 | Munakata et al. |
| 4,777,145 A | 10/1988 | Luotola et al. |
| 4,849,340 A | 7/1989 | Oberhardt |
| 4,865,997 A | 9/1989 | Stoker |
| 4,916,081 A | 4/1990 | Kamada et al. |
| 4,945,045 A | 7/1990 | Forrest et al. |
| 4,978,610 A | 12/1990 | Forrest et al. |
| 5,061,445 A | 10/1991 | Zoski et al. |
| 5,068,088 A | 11/1991 | Hall et al. |
| 5,093,268 A | 3/1992 | Leventis et al. |
| 5,112,646 A | 5/1992 | Koshi et al. |
| 5,115,534 A | 5/1992 | Fournier |
| 5,132,227 A | 7/1992 | Kelly |
| 5,147,806 A | 9/1992 | Kamin et al. |
| 5,189,549 A | 2/1993 | Leventis et al. |
| 5,238,808 A | 8/1993 | Bard et al. |
| 5,240,863 A | 8/1993 | Shibue et al. |
| 5,247,243 A | 9/1993 | Hall et al. |
| 5,296,191 A | 3/1994 | Hall et al. |
| 5,298,427 A | 3/1994 | Bobbitt et al. |
| 5,310,687 A | 5/1994 | Bard et al. |
| 5,324,457 A | 6/1994 | Zhang et al. |
| 5,429,893 A | 7/1995 | Thomas |
| 5,451,528 A | 9/1995 | Raymoure et al. |
| 5,466,416 A | 11/1995 | Ghaed et al. |
| 5,500,188 A | 3/1996 | Hafeman et al. |
| 5,538,687 A | 7/1996 | Kotzan et al. |
| 5,541,113 A | 7/1996 | Siddigi et al. |
| 5,543,112 A | 8/1996 | Ghead et al. |
| 5,589,136 A | 12/1996 | Northrup et al. |
| 5,624,637 A | 4/1997 | Ghaed et al. |
| 5,632,956 A | 5/1997 | Ghaed et al. |
| 5,700,427 A | 12/1997 | Ghaed et al. |
| 5,705,402 A | 1/1998 | Leland et al. |
| 5,716,842 A | 2/1998 | Baier et al. |
| 5,720,922 A | 2/1998 | Ghaed et al. |
| 5,744,367 A | 4/1998 | Talley et al. |
| 5,746,974 A | 5/1998 | Massey et al. |
| 5,779,976 A | 7/1998 | Leland et al. |
| 5,786,141 A | 7/1998 | Bard et al. |
| 5,798,083 A | 8/1998 | Massey et al. |
| 5,833,925 A | 11/1998 | Shu et al. |
| 5,935,779 A | 8/1999 | Massey et al. |
| 5,965,452 A | 10/1999 | Kovacs |
| 5,993,740 A | 11/1999 | Niiyama et al. |
| 6,036,840 A | 3/2000 | Christensen |
| 6,066,448 A | 5/2000 | Wohlstadter et al. |
| 6,078,782 A | 6/2000 | Leland et al. |
| 6,133,043 A | 10/2000 | Talley et al. |
| 6,136,268 A | 10/2000 | Ala-Kleme et al. |
| 6,200,531 B1 | 3/2001 | Liljestrand et al. |
| 6,207,369 B1 | 3/2001 | Wohlstadter et al. |
| 6,325,973 B1 | 12/2001 | Leland et al. |
| 6,479,233 B1 * | 11/2002 | Bard et al. ............ 435/6 |
| 6,517,777 B2 | 2/2003 | Liljestrand et al. |
| 2003/0118477 A1 * | 6/2003 | Liljestrand et al. ........... 422/52 |
| 2003/0186458 A1 * | 10/2003 | DiCesare et al. ............ 436/172 |
| 2007/0034529 A1 | 2/2007 | Bard et al. |

FOREIGN PATENT DOCUMENTS

| | | |
|---|---|---|
| EP | 0 247 796 A1 | 12/1987 |
| GB | 1 500 127 | 2/1978 |
| GB | 2 005 019 A | 4/1979 |
| GB | 2 074 727 A | 11/1981 |
| WO | WO 83/01687 | 5/1983 |
| WO | WO 83/01687 A1 | 5/1983 |
| WO | WO 85/00663 A1 | 2/1985 |
| WO | WO 85/01253 A1 | 3/1985 |
| WO | WO 86/02734 A1 | 5/1986 |
| WO | WO 86/05815 A1 | 10/1986 |
| WO | WO 87/00987 A1 | 2/1987 |
| WO | WO 87/06706 A1 | 11/1987 |
| WO | WO 87/07386 A1 | 12/1987 |
| WO | WO 88/03947 A1 | 6/1988 |
| WO | WO 89/01814 A1 | 3/1989 |
| WO | WO 89/04373 A1 | 5/1989 |
| WO | WO 89/04854 A1 | 6/1989 |
| WO | WO 89/04859 A1 | 6/1989 |
| WO | WO 89/04915 A2 | 6/1989 |
| WO | WO 89/04919 A2 | 6/1989 |
| WO | WO 90/01370 A1 | 2/1990 |
| WO | WO 92/14139 A1 | 8/1992 |
| WO | WO 93/01308 A1 | 1/1993 |
| WO | WO 93/05142 A1 | 3/1993 |
| WO | WO 98/12539 A1 | 3/1998 |
| WO | WO 99/14597 | 3/1999 |
| WO | WO 99/14597 A1 | 3/1999 |

OTHER PUBLICATIONS

Japanese Abstract of JP 1-247962 A, "Heat Pump", Hiroshi et al., Publication Date Oct. 3, 1989.

Krüger et al., "Electrochemical carbon nanotube field-effect transistor", *Applied Physics Letters*, vol. 78, No. 9, Feb. 26, 2001 (pp. 1291-1293).

Liu et al., "Electrochemistry and Electrogenerated Chemiluminescence with a Single Faradaic Electrode", *Analytical Chemistry*, vol. 77, No. 16, Aug. 15, 2005 (pp. 5339-5343).

Miao et al., "Electrogenerated Chemiluminescence 69: The Tris(2,2'-bipyridine)ruthenium(II), $(Ru(bpy)_3^{2+})$/Tri-$n$-propylamine (TPrA) System Revisited—A New Route Involving TPrA$^{\cdot+}$ Cation Radicals", *J. Am. Chem. Soc.*, vol. 124, No. 48, 2002 (pp. 14478-14485).

Xu et al., "Electrochemical study of ultrathin silica films supported on a platinum substrate", *J. Vac. Sci. Technol. A*, vol. 12, No. 4, Jul./Aug. 1994 (pp. 1882-1885).

Hansen et al., "A study of electrode immersion and emersion," *J. Electroanal. Chem.* vol. 93, 87-98 (1978).

Kolthoff et al., *Polarography*, Interscience Publishers, vol. 1 of 2, 357-371 (1952).

International Search Report of PCT/US2006/021488 (Apr. 7, 2007).

Krüger et al., "Electrochemical carbon nanotube field-effect transistor," *Appl. Phys. Lett.* 78(9):1291-1293 (2001).

Liu et al., "Electrochemistry and electrogenerated chemiluminescence with a single faradaic electrode," *Anal. Chem.* 77(16):5339-5343 (2005).

Miao et al., "Electrogenerated chemiluminescence 69: The Tris(2,2'-bipyridine)ruthenium(II), $(Ru(bpy)_3^{2+})$/Tri-$n$-propylamine(TPrA) system revisited—A new route involving TPrA$^+$ cation radicals," *J. Am. Chem. Soc.* 124(48):14478-14485 (2002).

Xu et al., "Electrochemical study of ultrathin silica films supported on a platinum substrate," *J. Vac. Sci. Tecnol. A.* 12(4):1882-1885 (1994).

* cited by examiner

ELECTROCHEMISTRY AND ELECTROGENERATED CHEMILUMINESCENCE WITH A SINGLE FARADAIC ELECTRODE

CROSS-REFERENCE TO RELATED APPLICATIONS

This application claims the benefit of U.S. provisional application No. 60/686,935, filed Jun. 3, 2005; U.S. provisional application No. 60/695,163, filed Jun. 30, 2005; and U.S. provisional application No. 60/737,472, filed Nov. 17, 2005, all of which are incorporated herein by reference in their entireties.

FIELD OF THE INVENTION

This invention relates to an electrochemical apparatus comprising an electrochemical cell with a faradaic working electrode and a capacitive counter electrode and methods of the cell's use. The electrochemical cell is useful for controlling the redox products generated and/or the timing of the redox product generation. In some embodiments, it is useful for generating electrochemiluminescence and methods of using the same.

BACKGROUND

Electrochemiluminescent (ECL) methods and systems are useful in a variety of applications including medical diagnostics, food and beverage testing, environmental monitoring, manufacturing quality control, drug discovery and basic scientific research. There are a number of commercially available instruments that utilize ECL for analytical measurements.

Species that can be induced to emit ECL (ECL moieties) have been used as ECL labels in various testing procedures. The light generated by ECL labels can be used as a reporter signal in diagnostic procedures (Bard et al., U.S. Pat. No. 5,238,808). For instance, an ECL label can be covalently coupled to a binding agent such as an antibody or a nucleic acid probe, and the participation of the binding reagent in a binding interaction can be monitored by measuring ECL emitted from the ECL label. Alternatively, the ECL signal from an ECL-active compound can be indicative of the chemical environment (see, e.g., U.S. Pat. No. 5,641,623 which describes ECL assays that monitor the formation or destruction of ECL coreactants).

For more background on ECL, ECL labels, ECL assays and instrumentation for conducting ECL assays see U.S. Pat. Nos. 5,093,268; 5,147,806; 5,324,457; 5,591,581; 5,597,910; 5,641,623; 5,643,713; 5,679,519; 5,705,402; 5,846,485; 5,866,434; 5,786,141; 5,731,147; 6,066,448; 6,136,268; 5,776,672; 5,308,754; 5,240,863; 6,207,369; and 5,589,136 and Published PCT Nos. WO99/63347; WO00/03233; WO99/58962; WO99/32662; WO99/14599; WO98/12539; WO97/36931 and WO98/57154.

Commercially available ECL instruments are widely used for reasons including their excellent sensitivity, dynamic range, precision, and tolerance of complex sample matrices. Many commercially available instruments use flow cell-based designs with permanent reusable flow cells. The use of a permanent flow cell provides many advantages but also some limitations, for example, in assay throughput. In some applications, for example, the screening of chemical libraries for potential therapeutic drugs, assay instrumentation should perform large numbers of analyses at high speeds on small quantities of samples.

A variety of techniques have been developed for increasing assay throughput and decreasing sample size. The use of multi-well assay plates allows for the parallel processing and analysis of multiple samples distributed in multiple wells of a plate. Typically, samples and reagents are stored, processed and/or analyzed in multi-well assay plates (also known as microplates or microtiter plates). Multi-well assay plates can take a variety of forms, sizes and shapes. For convenience, some standards have appeared for some instrumentation used to process samples for high throughput assays. Multi-well assay plates typically are made in standard sizes and shapes and with standard arrangements of wells. Some well established arrangements of wells include those found on 96-well plates (12×8 array of wells), 384-well plates (24×16 array of wells) and 1536-well plate (48×32 array of wells). The Society for Biomolecular Screening and ANSI have published microplate specifications for a variety of plate formats (see, http://www.sbsonline.org).

There is a need for ECL assay systems, and assays systems based on other electrochemical methods, that require lower sample volume, and are less expensive, faster, and more sensitive. As these assays move to the nanoscale to address these needs, it is increasingly difficult to separate the working electrode from the counter electrode: As the working and counter electrodes are brought closer together in the same cell, undesirable redox byproducts formed at the counter electrode can interact with species at the working electrode.

To date, cells using one capacitive and one faradaic electrode have been used in solid state systems, for example, to inject charge into thin layers of luminescent organic polymers to aid the observation of spectroscopic properties. In such systems, one electrode contacts the polymer layer and the other electrode is a small tip separated from the polymer layer by a ~10 nm insulating layer of impurities or air. See for example, Adams, et al., *J. Phys. Chem. B*, 2000,104, 6728. These cells are not electrochemical cells, do not use an electrolyte solution, and are not designed to contain an electrolyte solution. Configurations involving a capacitive electrode and a reference electrode have been used to examine double layer effects. See, for example, Grahame, *Chem. Rev.*, 1947, 41, 441. These studies focus on the importance of the polarized electrode. Any faradaic effects at the reference electrode were not of interest and were neglected.

There remains a need for an electrochemical apparatus that reduces the introduction of undesirable electrochemically generated byproducts into the sample.

There remains a need for an electrochemical apparatus that separately controls the timing of the generation of oxidation and reduction products.

SUMMARY OF THE INVENTION

The present invention provides an apparatus comprising an electrochemical cell comprising: a faradaic working electrode and a capacitive counter electrode wherein the electrochemical cell is capable of receiving an electrolyte solution that can simultaneously contact said faradaic working electrode and said capacitive counter electrode.

Also provided are methods of determining the presence or amount of an analyte in a sample comprising the steps of:
  (a) optionally preprocessing the sample;
  (b) contacting a faradaic working electrode to a solution comprising
    the optionally pre-processed sample; and an electrolyte;

(c) contacting a capacitive counter electrode to the solution;

(d) supplying electrical energy between the faradaic working electrode and the capacitive counter electrode sufficient to provide for faradaic charge transfer at the faradaic working electrode;

(e) measuring at least one of (i) light, (ii) current, (iii) voltage, and (iv) charge to determine the presence or amount of the analyte in the sample.

Also provided are methods of generating at least one electrochemical product at a working electrode while generating a discordantly smaller amount of electrochemical byproduct at a counter electrode, comprising the steps of:

contacting a faradaic working electrode with an electrolyte solution;

contacting a capacitive counter electrode with the electrolyte solution; and applying electrical energy between the faradaic working electrode and the capacitive counter electrode wherein the faradaic charge transferred across the faradaic working electrode is at least about 10 times the faradaic charge transferred across the capacitive counter electrode, thus generating a discordantly smaller amount of electrochemical byproduct at the counter electrode.

In this method and any methods disclosed or claimed herein, the faradaic and the capacitive electrodes may be placed in contacted with the electrolyte or sample solution in any order.

DETAILED DESCRIPTION OF THE INVENTION

Figure 1:
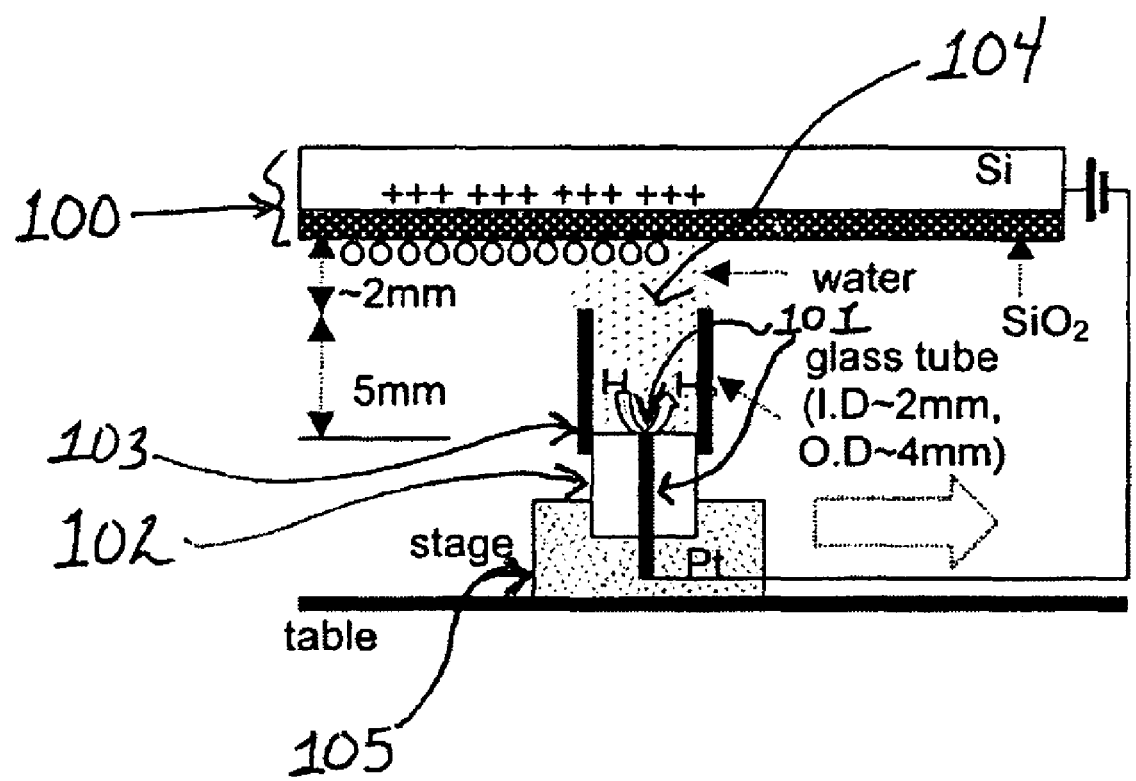
FIG. 1. Schematic diagram showing the system Pt/water/$SiO_2$/Si with the possibility of lateral tip movement to generate fresh contact surface. The tip was attached to a translation stage that could be moved with an inchworm motor, a micrometer, or by hand.

The following description refers to the accompanying drawings in which, in the absence of a contrary representation, the same numbers in different drawings represent similar elements. The implementations in the following description do not represent all implementations consistent with principles of the claimed invention. Instead, they are merely some examples of systems and methods consistent with those principles. It is to be understood that both the foregoing general description and the following detailed description are exemplary and explanatory only and are not restrictive of the invention as claimed.

I. Definitions

As used in the present specification, the following words and phrases are generally intended to have the meanings as set forth below, except to the extent that the context in which they are used indicates otherwise. These definitions are placed in this section for the reader's convenience. Definitions for other terms, words and phrases, which may be found in other sections of this application, also describe the intended meanings, except to the extent that the context in which they are used indicates otherwise.

A. General Definitions

The term "aliphatic," as used herein, is defined as in *The American Heritage® Dictionary of the English Language, Fourth Edition Copyright© 2000* and encompasses organic chemical compounds in which the carbon atoms are linked in open chains. The open chains comprise from 1 to 20 carbon atoms, or from 1 to 13, or from 1 to 6 carbon atoms. When an aliphatic group is unsaturated there can be from 1 to 10, or from 1 to 6, or from 1 to 3 points of unsaturation. The number of carbon atoms in an aliphatic group can be indicated by a subscript on a "C" (for example, "$C_3$ aliphatic" represents an aliphatic group comprising 3 carbon atoms). Likewise, ranges can be expressed in the subscript. For example "$C_{1-10}$ aliphatic" encompasses aliphatic groups of from 1 to 10 carbon atoms inclusive. Examples of aliphatic groups include, but are not limited to, methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, ethene, propene, ethyne, butene, propyne, butyne, and the like. When an aliphatic group having a specific number of carbons is named using the subscripted C notation, all isomers having that number of carbons are intended to be encompassed. Aliphatic groups can be optionally substituted by at least one hydrophilic functional group, as defined herein. In addition, aliphatic groups useful as ECL moieties and as ECL coreactants may also comprise additional functional groups and may have a single (i.e., monodentate ligand) or multiple (i.e., bidentate or polydentate ligands) points of attachment. Such aliphatic groups are well known in the art and are described in *Electrogenerated Chemiluminescence*, Bard, Editor, Marcel. Dekker, (2004); Knight, A and Greenway, G. *Analyst* 119: 879-890 1994.

The term "hydrophilic functional group" refers to a functional group that facilitates or that increases the solubility of a molecule in water. Examples include, but are not limited to, groups such as hydroxyl (—OH), aldehyde (—C(O)H), hydroxycarbonyl (—C(OH)(C═O)H), amino (—NH$_2$), aminocarbonyl (—CONH$_2$), amidine (—C(=NH)NH$_2$), imino (—C=NH), cyano (—CN), nitro (—NO$_2$), nitrate (—NO$_3$), sulfate (—SO$_4$), sulfonate (—SO$_3$H), phosphate (—PO$_4$), phosphonate (—PH$_2$O$_3$), silicate (—SiHO$_3$), carboxylate (—COOH), borate (—BH$_2$O$_3$), guanidinium (—HN—C (=NH)—NH$_2$), carbamide (—HNC(O)NH$_2$), carbamate (—HNC(O)NH$_2$), carbonate (—CO$_3$), sulfamide (—S(O)$_2$NH$_2$), silyl (—SiH$_3$ and/or —Si(OH)$_3$), siloxy (—OSiH$_3$ and/or —OSi(OH)$_3$), amide and the like.

The term "binding partner," as used herein, means a substance that can bind specifically to an analyte of interest. In general, specific binding is characterized by a relatively high affinity and a relatively low to moderate capacity. Nonspecific binding usually has a low affinity with a moderate to high capacity. Typically, binding is considered specific when the affinity constant Ka is higher than about $10^6$ M$^{-1}$. For example, binding may be considered specific when the affinity constant Ka is higher than about $10^8$ M$^{-1}$. A higher affinity constant indicates greater affinity, and thus typically greater specificity. For example, antibodies typically bind antigens with an affinity constant in the range of $10^6$ M$^{-1}$ to $10^9$ M$^{-1}$ or higher.

Examples of binding partners include complementary nucleic acid sequences (e.g., two DNA sequences which hybridize to each other; two RNA sequences which hybridize to each other; a DNA and an RNA sequence which hybridize to each other), an antibody and an antigen, a receptor and a ligand (e.g., TNF and TNFr-I, CD142 and Factor VIIa, B7-2 and CD28, HIV-1 and CD4, ATR/TEM8 or CMG and the protective antigen moiety of anthrax toxin), an enzyme and a substrate, or a molecule and a binding protein (e.g., vitamin B12 and intrinsic factor, folate and folate binding protein).

As mentioned above, antibodies are an example of a binding partner. The term "antibody," as used herein, means an immunoglobulin or a part thereof, and encompasses any polypeptide (with or without further modification by sugar moieties (mono and polysaccharides)) comprising an antigen binding site regardless of the source, method of production, or other characteristics. The term includes, for example, polyclonal, monoclonal, monospecific, polyspecific, humanized, single chain, chimeric, synthetic, recombinant, hybrid, mutated, and CDR grafted antibodies as well as fusion proteins. A part of an antibody can include any fragment which can bind antigen, including but not limited to Fab, Fab', F(ab')$_2$, Facb, Fv, ScFv, Fd, V$_H$, and V$_L$.

A large number of monoclonal antibodies that bind to various analytes of interest are available, as exemplified by the listings in various catalogs, such as: Biochemicals and Reagents for Life Science Research, Sigma-Aldrich Co., P.O. Box 14508, St. Louis, Mo., 63178 (1999); the Life Technologies Catalog, Life Technologies, Gaithersburg, Md.; and the Pierce Catalog, Pierce Chemical Company, P.O. Box 117, Rockford, Ill. 61105 (1994).

Other exemplary monoclonal antibodies include those that bind specifically to β-actin, DNA, digoxin, insulin, progesterone, human leukocyte markers, human interleukin-10, human interferon, human fibrinogen, p53, hepatitis B virus or a portion thereof, HIV virus or a portion thereof, tumor necrosis factor, or FK-506. In certain embodiments, the monoclonal antibody is chosen from antibodies that bind specifically to at least one of T4, T3, free T3, free T4, TSH (thyroid-stimulating hormone), thyroglobulin, TSH receptor, prolactin, LH (luteinizing hormone), FSH (follicle stimulating hormone), testosterone, progesterone, estradiol, hCG (human Chorionic Gondaotropin), hCG+β, SHBG (sex hormone-binding globulin), DHEA-S (dehydroepiandrosterone sulfate), hGH (human growth hormone), ACTH (adrenocorticotropic hormone), cortisol, insulin, ferritin, folate, RBC (red blood cell) folate, vitamin B12, vitamin D, C-peptide, troponin T, CK MB (creatine kinase-myoglobin), myoglobin, pro-BNP (brain natriuretic peptide), HbsAg (hepatitis B surface antigen), HbeAg (hepatitis Be antigen), HIV antigen, HIV combined, H. pylori, β-CrossLaps, osteocalcin, PTH (parathyroid hormone), IgE, digoxin, digitoxin, AFP (α-fetoprotein), CEA (carcinoembryonic antigen), PSA (prostate specific antigen), free PSA, CA (cancer antigen) 19-9, CA 12-5, CA 72-4, cyfra 21-1, NSE (neuron specific enolase), S-100, P1NP (procollagen type 1 N-propeptide), PAPP-A (pregnancy-associated plasma protein-A), Lp-PLA2 (lipoprotein-associated phospholipase A2), sCD40L (soluble CD40 Ligand), IL 18, and Survivin.

Other exemplary monoclonal antibodies include anti-TPO (antithyroid peroxidase antibody), anti-HBc (Hepatitis Bc antigen), anti-HBc/IgM, anti-HAV (hepatitis A virus), anti-HAV/IgM, anti-HCV (hepatitis C virus), anti-HIV, anti-HIV p-24, anti-rubella IgG, anti-rubella IgM, anti-toxoplasmosis IgG, anti-toxoplasmosis IgM, anti-CMV (cytomegalovirus) IgG, anti-CMV IgM, anti-HGV (hepatitis G virus), and anti-HTLV (human T-lymphotropic virus).

Further examples of binding partners include binding proteins, for example, vitamin B12 binding protein, DNA binding proteins such as the superclasses of basic domains, zinc-coordinating DNA binding domains, Helix-turn-helix, beta scaffold factors with minor groove contacts, and other transcription factors that are not antibodies.

The term "labeled binding partner," as used herein, means a binding partner that is labeled with an atom, moiety, functional group, or molecule capable of generating, modifying or modulating a detectable signal. For example, in a radiochemical assay, the labeled binding partner may be labeled with a radioactive isotope of iodine. Alternatively, the labeled binding partner antibody may be labeled with an enzyme—e.g., horseradish peroxidase—that can be used in a colorimetric assay. The labeled binding partner may also be labeled with a fluorophore, such as one useful in fluorescence measurements, time-resolved fluorescence measurements or a fluorescence resonance energy transfer (FRET) measurements. Exemplary reporters are disclosed in Hemmila, et al., J. Biochem. Biophys. Methods, vol. 26, pp. 283-290 (1993); Kakabakos, et al., Clin. Chem., vol. 38, pp. 338-342 (1992); Xu, et al., Clin. Chem., pp. 2038-2043 (1992); Hemmila, et al., Scand. J. Clin. Lab. Invest., vol. 48, pp. 389-400 (1988); Bioluminescence and Chemiluminescence Proceedings of the 9th International Symposium 1996, J. W. Hastings, et al., Eds., Wiley, New York, 1996; Bioluminescence and Chemiluminescence Instruments and Applications, Knox Van Dyre, Ed., CRC Press, Boca Raton, 1985; I. Hemmila, Applications of Fluorescence in Immunoassays, Chemical Analysis, Volume 117, Wiley, New York, 1991; and Blackburn, et al., Clin. Chem., vol. 37, p. 1534 (1991).

Further examples of labeled binding partners include binding partners that are labeled with an electrochemiluminescent moiety (ECL moiety), functional group, or molecule that is useful for generating a signal in an electrochemiluminescent (ECL) assay. The ECL moiety may be any compound that can be induced to repeatedly emit electromagnetic radiation by direct exposure to an electrical energy source. Such moieties, functional groups, or molecules are disclosed in U.S. Pat. Nos. 5,962,218; 5,945,344; 5,935,779; 5,858,676; 5,846,485; 5,811,236; 5,804,400; 5,798,083; 5,779,976; 5,770,459; 5,746,974; 5,744,367; 5,731,147; 5,720,922; 5,716,781; 5,714,089; 5,705,402; 5,700,427; 5,686,244; 5,679,519; 5,643,713; 5,641,623; 5,632,956; 5,624,637; 5,610,075; 5,597,910; 5,591,581; 5,543,112; 5,466,416; 5,453,356;

5,310,687; 5,296,191; 5,247,243; 5,238,808; 5,221,605; 5,189,549; 5,147,806; 5,093,268; 5,068,088; 5,061,445; and 6,808,939; Dong, L. et al., Anal. Biochem., vol. 236, pp. 344-347 (1996); Blohm, et al., Biomedical Products, vol. 21, No. 4: 60 (1996); Jameison, et al., Anal. Chem., vol. 68, pp. 1298-1302 (1996); Kibbey, et al., Nature Biotechnology, vol. 14, no. 3, pp. 259-260 (1996); Yu, et al., Applied and Environmental Microbiology, vol. 62, no. 2, pp. 587-592 (1996); Williams, American Biotechnology, p. 26 (January, 1996); Darsley, et al., Biomedical Products, vol. 21, no. 1, p. 133 (January, 1996); Kobrynski, et al., Clinical and Diagnostic Laboratory Immunology, vol. 3, no. 1, pp. 42-46 (January 1996); Williams, IVD Technology, pp. 28-31 (November, 1995); Deaver, Nature, vol. 377, pp. 758-760 (Oct. 26, 1995); Yu, et al., BioMedical Products, vol. 20, no. 10, p. 20 (October, 1995); Kibbey, et al., BioMedical Products, vol. 20, no. 9, p. 116 (September, 1995); Schutzbank, et al., Journal of Clinical Microbiology, vol. 33, pp. 2036-2041 (August, 1995); Stern, et al., Clinical Biochemistry, vol. 28, pp. 470-472 (August, 1995); Carlowicz, Clinical Laboratory News, vol. 21, no. 8, pp. 1-2 (August 1995); Gatto-Menking, et al., Biosensors & Bioelectronics, vol. 10, pp. 501-507 (July, 1995); Yu, et al., Journal of Bioluminescence and Chemiluminescence, vol. 10, pp. 239-245 (1995); Van Gemen, et al., Journal of Virology Methods, vol. 49, pp. 157-167 (1994); Yang, et al., Bio/Technology, vol. 12, pp. 193-194 (1994); Kenten, et al., Clinical Chemistry, vol. 38, pp. 873-879 (1992); Kenten, Non-radioactive Labeling and Detection of Biomolecules, Kessler, Ed., Springer, Berlin, pp. 175-179 (1992); Gudibande, et al., Journal of Molecular and Cellular Probes, vol. 6, pp. 495-503 (1992); Kenten, et al., Clinical Chemistry, vol. 37, pp. 1626-1632 (1991); Blackburn, et al., Clinical Chemistry, vol. 37, pp. 1534-1539 (1991), Electrogenerated Chemiluminescence, Bard, Editor, Marcel Dekker, (2004), and U.S. Pat. No. 5,935,779. In certain embodiments, the electrochemiluminescent group can comprise a metal, such as ruthenium or osmium. In certain embodiments, the binding partner can be labeled with a ruthenium moiety, such as a tris-bipyridyl-ruthenium group such as ruthenium (II) tris-bipyridine ($[Ru(bpy)_3]^{2+}$).

The term "analyte," as used herein, means any molecule, or aggregate of molecules, including a cell or a cellular component of a virus, found in a sample. Examples of analytes to which the binding partner can specifically bind include bacterial toxins, viruses, bacteria, proteins, hormones, DNA, RNA, drugs, antibiotics, nerve toxins, and metabolites thereof. Also included in the scope of the term "analyte" are fragments of any molecule found in a sample. An analyte may be an organic compound, an organometallic compound or an inorganic compound. An analyte may be a nucleic acid (e.g., DNA, RNA, a plasmid, a vector, or an oligonucleotide), a protein (e.g., an antibody, an antigen, a receptor, a receptor ligand, or a peptide), a lipoprotein, a glycoprotein, a ribo- or deoxyribonucleoprotein, a peptide, a polysaccharide, a lipopolysaccharide, a lipid, a fatty acid, a vitamin, an amino acid, a pharmaceutical compound (e.g., tranquilizers, barbiturates, opiates, alcohols, tricyclic antidepressants, benzodiazepines, anti-virals, anti-fungals, antibiotics, steroids, cardiac glycosides, or a metabolite of any of the preceding), a hormone, a growth factor, an enzyme, a coenzyme, an apoenzyme, a hapten, a lectin, a substrate, a cellular metabolite, a cellular component or organelle (e.g., a membrane, a cell wall, a ribosome, a chromosome, a mitochondria, or a cytoskeleton component). Also included in the definition are toxins, pesticide, herbicides, and environmental pollutants. The definition further includes complexes comprising one or more of any of the examples set forth within this definition.

Further examples of analytes include bacterial pathogens such as *Aeromonas hydrophila* and other species (spp.); *Bacillus anthracis; Bacillus cereus*; Botulinum neurotoxin producing species of *Clostridium; Brucella abortus; Brucella melitensis; Brucella suis; Burkholderia mallei* (formally *Pseudomonas mallei*); *Burkholderia pseudomallei* (formerly *Pseudomonas pseudomallei*); *Campylobacter jejuni; Chlamydia psittaci; Clostridium botulinum; Clostridium perfringens; Cowdria ruminantium* (Heartwater); *Coxiella burnetii*; Enterovirulent *Escherichia coli* group (EEC Group) such as *Escherichia coli*—enterotoxigenic (ETEC), *Escherichia coli*—enteropathogenic (EPEC), *Escherichia coli*—O157:H7 enterohemorrhagic (EHEC), and *Escherichia coli*—enteroinvasive (EIEC); *Ehrlichia* spp. such as *Ehrlichia chaffeensis; Francisella tularensis; Legionella pneumophilia; Liberobacter africanus; Liberobacter asiaticus; Listeria monocytogenes*; miscellaneous enterics such as *Klebsiella, Enterobacter, Proteus, Citrobacter, Aerobacter, Providencia*, and *Serratia; Mycobacterium bovis; Mycobacterium tuberculosis; Mycoplasma capricolum; Mycoplasma mycoides* ssp *mycoides; Peronosclerospora philippinensis; Phakopsora pachyrhizi; Plesiomonas shigelloides; Ralstonia solanacearum* race 3, biovar 2; *Rickettsia prowazekii; Rickettsia rickettsii; Salmonella* spp.; *Schlerophthora rayssiae var zeae; Shigella* spp.; *Staphylococcus aureus; Streptococcus; Synchytrium endobioticum*; Vibrio cholerae non-O1; Vibrio cholerae O1; Vibrio parahaemolyticus and other Vibrios; *Vibrio vulnificus; Xanthomonas oryzae; Xylella fastidiosa* (citrus variegated chlorosis strain); *Yersinia enterocolitica* and *Yersinia pseudotuberculosis*; and *Yersinia pestis*.

Further examples of analytes include viruses such as African horse sickness virus; African swine fever virus; Akabane virus; Avian influenza virus (highly pathogenic); Bhanja virus; Blue tongue virus (Exotic); Camel pox virus; Cercopithecine herpesvirus 1; Chikungunya virus; Classical swine fever virus; Coronavirus (SARS); Crimean-Congo hemorrhagic fever virus; Dengue viruses; Dugbe virus; Ebola viruses; Encephalitic viruses such as Eastern equine encephalitis virus, Japanese encephalitis virus, Murray Valley encephalitis, and Venezuelan equine encephalitis virus; Equine morbillivirus; Flexal virus; Foot and mouth disease virus; Germiston virus; Goat pox virus; Hantaan or other Hanta viruses; Hendra virus; Issyk-kul virus; Koutango virus; Lassa fever virus; Louping-ill virus; Lumpy skin disease virus; Lymphocytic choriomeningitis virus; Malignant catarrhal fever virus (Exotic); Marburg virus; Mayaro virus; Menangle virus; Monkeypox virus; Mucambo virus; Newcastle disease virus (VVND); Nipah Virus; Norwalk virus group; Oropouche virus; Orungo virus; Peste Des Petits Ruminants virus; Piry virus; Plum Pox Potyvirus; Poliovirus; Potato virus; Powassan virus; Rift Valley fever virus; Rinderpest virus; Rotavirus; Semliki Forest virus; Sheep pox virus; South American hemorrhagic fever viruses such as Flexal, Guanarito, Junin, Machupo, and Sabia; Spondweni virus; Swine vesicular disease virus; Tick-borne encephalitis complex (flavi) viruses such as Central European tick-borne encephalitis, Far Eastern tick-borne encephalitis, Russian spring and summer encephalitis, Kyasanur forest disease, and Omsk hemorrhagic fever; Variola major virus (Smallpox virus); Variola minor virus (Alastrim); Vesicular stomatitis virus (Exotic); Wesselbron virus; West Nile virus; Yellow fever virus; viruses from the family papovaviridae, including polyomaviruses such as SV40, JC and BK and including papillomaviruses (e.g., HPV); parvoviruses (e.g., B19 and RA-1); and viruses from the family Picornaviridae, including rhinoviruses and Coxsackie B. Other viruses that can comprise a target nucleic acid sequence include species not mentioned above belonging to the families Adenoviridae, Arenaviridae, Arterivirus, Astroviridae, Baculoviridae, Badnavirus, Bamaviridae, Birnaviridae, Bromoviridae, Bunyaviridae, Caliciviridae, Capillovirus, Carla virus, Caulimovirus, Circoviridae, Closterovirus, Comoviridae, Coronaviridae, Corticoviridae, Cystoviridae, Deltavirus, Dianthovirus, Enamovirus, Filoviridae, Flaviviridae, Furovirus, Fuselloviridae, Geminiviridae, Hepadnaviridae, Herpesviridae, Hordeivirus, Hypoviridae, Idaeovirus, Inoviridae, Iridoviridae, Leviviridae, Lipothrixviridae, Luteoviridae, Machlomovirus, Marafivirus, Microviridae, Myoviridae, Necrovirus, Nodaviridae, Orthomyxoviridae, Paramyxoviridae, Partitiviridae, Parvoviridae, Phycodnaviridae, Plasmaviridae, Podoviridae, Polydnaviridae, Potexvirus, Potyviridae, Poxviridae, Reoviridae, Retroviridae, Rhabdoviridae, Rhizidiovirus, Sequiviridae, Siphoviridae, Sobemovirus, Tectiviridae, Tenuivirus, Tetraviridae, Tobamovirus, Tobravirus, Togaviridae, Tombusviridae, Totiviridae, Tymovirus, and Umbra virus.

Further examples of analytes include toxins such as Abrin; Aflatoxins; *Botulinum* neurotoxin; *Ciguatera* toxins; *Clostridium perfringens* epsilon toxin; Conotoxins; Diacetoxyscirpenol; *Diphtheria* toxin; Grayanotoxin; mushroom toxins such as amanitins, gyromitrin, and orellanine; Phytohaemagglutinin; Pyrrolizidine alkaloids; Ricin; shellfish toxins (paralytic, diarrheic, neurotoxic or amnesic) such as saxitoxin, akadaic acid, dinophysis toxins, pectenotoxins, yessotoxins, brevetoxins, and domoic acid; Shigatoxins; Shiga-like ribosome inactivating proteins; snake toxins; Staphylococcal enterotoxins; T-2 toxin; and Tetrodotoxin.

Further examples of analytes include prion proteins such as the Bovine spongiform encephalopathy agent.

Further examples of analytes include parasitic protozoa and worms, such as: *Acanthamoeba* and other free-living amoebae; *Anisakis* sp. and other related worms *Ascaris lumbricoides* and *Trichuris trichiura*; *Cryptosporidium parvum*; *Cyclospora cayetanensis*; *Diphyllobothrium* spp.; *Entamoeba histolytica*; *Eustrongylides* spp.; *Giardia lamblia*; *Nanophyetus* spp.; *Shistosoma* spp.; *Toxoplasma gondii*; and *Trichinella*.

Further examples of analytes include fungi such as: *Aspergillus* spp.; *Blastomyces dermatitidis*; *Candida*; *Coccidioides immitis*; *Coccidioides posadasii*; *Cryptococcus neoformans*; *Histoplasma capsulatum*; Maize rust; Rice blast; Rice brown spot disease; Rye blast; *Sporothrix schenckii*; and wheat fungus.

Further examples of analytes include genetic elements, recombinant nucleic acids, and recombinant organisms, such as (1) nucleic acids (synthetic or naturally derived, contiguous or fragmented, in host chromosomes or in expression vectors) that can encode infectious and/or replication competent forms of any of the select agents.

(2) nucleic acids (synthetic or naturally derived) that encode the functional form(s) of any of the toxins listed if the nucleic acids
  (i) are in a vector or host chromosome;
  (ii) can be expressed in vivo or in vitro; or
  (iii) are in a vector or host chromosome and can be expressed in vivo or in vitro;

(3) nucleic acid—protein complexes that are locations of cellular regulatory events:
  (i) viral nucleic acid—protein complexes that are precursors to viral replication;
  (ii) RNA-protein complexes that modify RNA structure and regulate protein transcription events; or
  (iii) Nucleic acid—protein complexes that are regulated by hormones or secondary cell signaling molecules.

(4) viruses, bacteria, fungi, and toxins that have been genetically modified.

Further examples of analytes include immune response molecules to the above-mentioned analyte examples such as IgA, IgD, IgE, IgG, and IgM.

The term "analog of the analyte," as used herein, refers to a substance that competes with the analyte of interest for binding to a binding partner. An analog of the analyte may be a known amount of the analyte of interest itself that is added to compete for binding to a specific binding partner with analyte of interest present in a sample. Examples of analogs of the analyte include azidothymidine (AZT), an analog of a nucleotide which binds to HIV reverse transcriptase, puromycin, an analog of the terminal aminoacyl-adenosine part of aminoacyl-tRNA, and methotrexate, an analog of tetrahydrofolate. Other analogs may be derivatives of the analyte of interest. The term "labeled analog of the analyte", as used herein, is defined in an analogous manner to labeled binding partner.

As used herein, the term "support," refers to any of the ways for immobilizing binding partners that are known in the art, such as membranes, beads, particles, electrodes, or even the walls or surfaces of a container. The support may comprise any material on which the binding partner is conventionally immobilized, such as nitrocellulose, polystyrene, polypropylene, polyvinyl chloride, EVA, glass, carbon, glassy carbon, carbon black, carbon nanotubes or fibrils, platinum, palladium, gold, silver, silver chloride, iridium, rhodium, or alloys comprising the metallic elements in this list. In one embodiment, the support is a bead, such as a polystyrene bead or a magnetizable bead. As used herein, the term "magnetizable bead" encompasses magnetic, paramagnetic, and superparamagnetic beads and/or particles. In various embodiments, beads can have a number of different sizes, for example, larger than about 3 mm, smaller than about 3 mm, smaller than about 1 mm, smaller than about 0.1 mm, smaller than about 100 µm, smaller than about 10 µm, smaller than about 5 µm, about 2.8 µm, about 1 µm, smaller than about 1 µm, smaller than about 0.5 µm, about 0.1 µm, or smaller than about 0.1 µm. Bead size can range from about 0.1 µm to about 5 mm, or from about 0.1 µm to about 3 mm, or from about 1 µm to about 3 µm, or from about 2.8 µm to about 5 µm. Combinations of beads sizes can also be used. In one embodiment, the support is a microcentrifuge tube or at least one well of a multiwell plate.

The term "dry composition," as used herein, means that the composition has a moisture content of less than or equal to about 5% by weight, relative to the total weight of the composition. Examples of dry compositions include compositions that have a moisture content of less than or equal to about 3% by weight relative to the total weight of the composition, of less than or equal to about 1% by weight relative to the total weight of the composition and compositions that have a moisture content ranging from about 1% to about 3% by weight, relative to the total weight of the composition.

In some embodiments of the present invention, the assay-performance-substance is a dry composition. In some embodiments of the present invention, the ECL moiety is a dry composition.

The term "sample," as used herein, comprises liquids that can contain the analyte. The term "liquid," as used herein, comprises—in addition to the more traditional definition of liquid-colloids, suspensions, slurries, and dispersions of particles in a liquid wherein the particles have a sedimentation rate due to earth's gravity of less than about 1 mm/s. The sample can be drawn from any source upon which analysis is desired. For example, the sample can arise from body or other biological fluid, such as blood, plasma, serum, milk, semen, amniotic fluid, cerebral spinal fluid, sputum, bronchoalveolar lavage, tears, saliva, urine, or stool. Alternatively, the sample can be a water sample obtained from a body of water, such as lake or river. The sample can also be prepared by dissolving or suspending a sample in a liquid, such as water or an aqueous buffer. The sample source can be a surface swab; for example, a surface can be swabbed; the swab washed by a liquid; thereby transferring an analyte from the surface into the liquid. The sample source can be air; for example, the air can be filtered; the filter washed by a liquid; thereby transferring an analyte from the air into the liquid.

The term "sample matrix," as used herein, refers to everything in the sample with the exception of the analyte.

The term "magnetic field source," as used herein, includes permanent magnets and electromagnets, which are separate, individual entities with defined N-S magnetic poles. A "dipole magnet" comprises one magnetic field source.

The term "sandwich magnet," as used herein, refers to magnets comprising two or more magnetic field sources configured such that their opposing magnetic fields overlap or are coerced. This can be accomplished by placing opposing poles (N-N or S-S) in closer proximity to each other than the attracting poles (N-S) of the magnetic fields sources. For example, two dipole magnets arranged in a N-S-S-N or a S-N-N-S configuration would form a sandwich magnet.

The term "channel magnet," as used herein, refers to a single magnetic field source bonded to a highly magnetizable material in the form of a U-shaped channel. In such a configuration, the magnetizable material becomes an extension of the magnetic pole to which it is bound.

B. ECL Moieties

The term "ECL moiety" refers to an electrochemiluminescent moiety, which is any compound that can be induced to repeatedly emit electromagnetic radiation by exposure to an electrical energy source. Representative ECL moieties are described in *Electrogenerated Chemiluminescence*, Bard, Editor, Marcel Dekker, (2004); Knight, A and Greenway, G. Analyst 119:879-890 1994; and in U.S. Pat. Nos. 5,221,605; 5,591,581; 5,858,676; and 6,808,939. Preparation of primers comprising ECL moieties is well known in the art, as described, for example, in U.S. Pat. No. 6,174,709. Some ECL moieties emit electromagnetic radiation is the visible spectrum while other might emit other types of electromagnetic radiation, such as infrared or ultraviolet light, X-rays, microwaves, etc. Use of the terms "electrochemiluminescence", "electrochemiluminescent", "electrochemiluminesce", "luminescence", "luminescent" and "luminesce" in connection with the present invention does not require that the emission be light, but includes the emission being such other forms of electromagnetic radiation.

ECL moieties can be transition metals. For example, the ECL moiety can comprise a metal-containing organic compound wherein the metal can be chosen, for example, from ruthenium, osmium, rhenium, iridium, rhodium, platinum, palladium, molybdenum, and technetium. For example, the metal can be ruthenium or osmium. For example, the ECL moiety can be a ruthenium chelate or an osmium chelate. For example, the ECL moiety can comprise bis(2,2'-bipyridyl)ruthenium(II) and tris(2,2'-bipyridyl)ruthenium(II). For example, the ECL moiety can be ruthenium (II) tris bipyridine ([Ru(bpy)$_3$]$^{2+}$). The metal can also be chosen, for example, from rare earth metals, including but not limited to cerium, dysprosium, erbium, europium, gadolinium, holmium, lanthanum, lutetium, neodymium, praseodymium, promethium, terbium, thulium, and ytterbium. For example, the metal can be cerium, europium, terbium, or ytterbium.

Metal-containing ECL moieties can have the formula

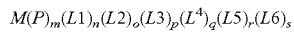

$$M(P)_m(L1)_n(L2)_o(L3)_p(L^4)_q(L5)_r(L6)_s$$

wherein M is a metal; P is a polydentate ligand of M; L1, L2, L3, L4, L5 and L6 are ligands of M, each of which can be the same as, or different from, each other; m is an integer equal to or greater than 1; each of n, o, p, q, r and s is an integer equal to or greater than zero; and P, L1, L2, L3, L4, L5 and L6 are of such composition and number that the ECL moiety can be induced to emit electromagnetic radiation and the total number of bonds to M provided by the ligands of M equals the coordination number of M. For example, M can be ruthenium. Alternatively, M can be osmium.

Some examples of the ECL moiety can have one polydentate ligand of M. The ECL moiety can also have more than one polydentate ligand. In examples comprising more than one polydentate ligand of M, the polydentate ligands can be the same or different. Polydentate ligands can be aromatic or aliphatic ligands. Suitable aromatic polydentate ligands can be aromatic heterocyclic ligands and can be nitrogen-containing, such as, for example, bipyridyl, bipyrazyl, terpyridyl, 1,10 phenanthroline, and porphyrins.

Suitable polydentate ligands can be unsubstituted, or substituted by any of a large number of substituents known to the art. Suitable substituents include, but are not limited to, alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, maleimide sulfur-containing groups, phosphorus-containing groups, and the carboxylate ester of N-hydroxysuccinimide.

In some embodiments, at least one of L1, L2, L3, L4, L5 and L6 can be a polydentate aromatic heterocyclic ligand. In various embodiments, at least one of these polydentate aromatic heterocyclic ligands can contain nitrogen. Suitable polydentate ligands can be, but are not limited to, bipyridyl, bipyrazyl, terpyridyl, 1,10 phenanthroline, a porphyrin, substituted bipyridyl, substituted bipyrazyl, substituted terpyridyl, substituted 1,10 phenanthroline or a substituted porphyrin. These substituted polydentate ligands can be substituted with an alkyl, substituted alkyl, aryl, substituted aryl, aralkyl, substituted aralkyl, carboxylate, carboxaldehyde, carboxamide, cyano, amino, hydroxy, imino, hydroxycarbonyl, aminocarbonyl, amidine, guanidinium, ureide, maleimide a sulfur-containing group, a phosphorus-containing group or the carboxylate ester of N-hydroxysuccinimide.

Some ECL moieties can contain two bidentate ligands, each of which can be bipyridyl, bipyrazyl, terpyridyl, 1,10 phenanthroline, substituted bipyridyl, substituted bipyrazyl, substituted terpyridyl or substituted 1,10 phenanthroline.

Some ECL moieties can contain three bidentate ligands, each of which can be bipyridyl, bipyrazyl, terpyridyl, 1,10-phenanthroline, substituted bipyridyl, substituted bipyrazyl, substituted terpyridyl or substituted 1,10-phenanthroline. For example, the ECL moiety can comprise ruthenium, two bidentate bipyridyl ligands, and one substituted bidentate bipyridyl ligand. For example, the ECL moiety can contain a tetradentate ligand such as a porphyrin or substituted porphyrin.

In some embodiments, the ECL moiety can have one or more monodentate ligands, a wide variety of which are known to the art. Suitable monodentate ligands can be, for example, carbon monoxide, cyanides, isocyanides, halides, and aliphatic, aromatic and heterocyclic phosphines, amines, stibines, and arsines.

In some embodiments, one or more of the ligands of M can be attached to additional chemical labels, such as, for example, radioactive isotopes, fluorescent components, or additional luminescent ruthenium- or osmium-containing centers.

For example, the ECL moiety can be tris(2,2'-bipyridyl) ruthenium(II) tetrakis(pentafluorophenyl)borate. For example, the ECL moiety can be bis[(4,4'-carbomethoxy-2, 2'-bipyridine] 2-[3-(4-methyl-2,2'-bipyridine-4-yl)propyl]-1,3-dioxolane ruthenium (II). For example, the ECL moiety can be bis(2,2'bipyridine) [4-(butan-1-al)-4'-methyl-2,2'-bipyridine]ruthenium (II). For example, the ECL moiety can be bis(2,2'-bipyridine) [4-(4'-methyl-2,2'-bipyridine-4'-yl)-butyric acid]ruthenium (II). For example, the ECL moiety can be (2,2'-bipyridine)[cis-bis(1,2-diphenylphosphino)ethylene]{2-[3-(4-methyl-2,2'-bipyridine-4'-yl)propyl]-1,3-dioxolane}osmium (II). For example, the ECL moiety can be bis(2,2'-bipyridine) [4-(4'-methyl-2,2'-bipyridine)-butylamine]ruthenium (II). For example, the ECL moiety can be bis(2,2'-bipyridine) [1-bromo-4(4'-methyl-2,2'-bipyridine-4-yl)butane]ruthenium (II). For example, the ECL moiety can be bis(2,2'-bipyridine)maleimidohexanoic acid, 4-methyl-2, 2'-bipyridine-4'-butylamide ruthenium (II).

In some embodiments of the present invention, an assay-performance-substance is used, wherein the assay-performance-substance comprises (i) an ECL moiety and (ii) a labeled binding partner for an analyte or a labeled analog of the analyte.

In some embodiments of the present invention, the assay-performance-substance comprises an ECL moiety.

In some embodiments, the ECL moiety comprises a metal ion selected from osmium and ruthenium.

In some embodiments, the ECL moiety comprises a derivative of trisbipyridyl ruthenium (II) [Ru(bpy)$_3^{2+}$].

In some embodiments, the ECL moiety can be [Ru(sulfo-bpy)$_2$bpy]$^{2+}$ whose structure is

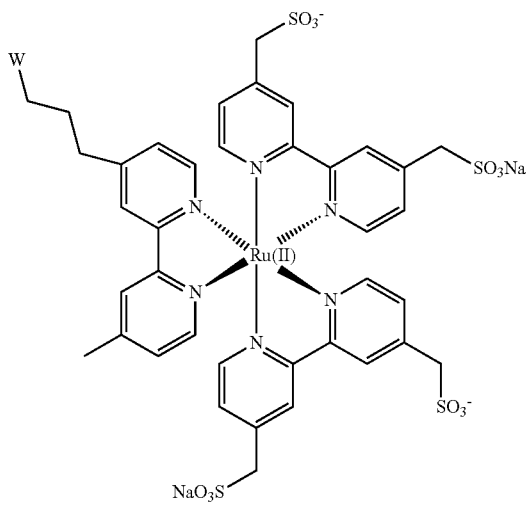

wherein W is a functional group such as an NHS ester, an activated carboxyl, an amino group, a hydroxyl group, a carboxyl group, a hydrazide, a maleimide, or a phosphoramidite. This functional group can react with a biological material, binding reagent, enzyme substrate or other assay reagent to form a covalent linkage.

In some embodiments, the ECL moiety does not comprise a metal. Such non-metal ECL moieties can be, but are not limited to, rubrene and 9,10-diphenylanthracene.

C. ECL Coreactant

The tem "ECL coreactant," as used herein, pertains to a chemical compound that either by itself or via its electrochemical reduction oxidation product(s), plays a role in the ECL reaction sequence. For simplicity, as used herein, ECL coreactants are described without regard to acid-base reactions; all acid-base forms of the stated compounds are also contemplated and claimed.

Often ECL coreactants can permit the use of simpler means for generating ECL (e.g., the use of only half of the double-step oxidation-reduction cycle) and/or improved ECL intensity. In some embodiments, ECL coreactants can be chemical compounds which, upon electrochemical oxidation/reduction, yield, directly or upon further reaction, strong oxidizing or reducing species in solution. An ECL coreactant can be peroxodisulfate (i.e., $S_2O_8^{2-}$, persulfate) which is irreversibly electro-reduced to form oxidizing $SO_4.^-$ ions. The ECL coreactant can also be oxalate (i.e., $C_2O_4^{2-}$) which is irreversibly electro-oxidized to form reducing $CO_2.^-$ ions. A class of ECL coreactants that can act as reducing agents is amines or compounds containing amine groups, including, for example, tri-n-propylamine (i.e., $N(CH_2CH_2CH_3)_3$, TPA). In some embodiments, tertiary amines can be better ECL coreactants than secondary amines. In some embodiments, secondary amines can be better ECL coreactants than primary amines.

In some embodiments, the electrochemical cell of the present invention further comprises an ECL coreactant.

In some embodiments, the ECL coreactant comprises a tertiary amine.

In some embodiments, the ECL coreactant comprises a tertiary amine comprising a hydrophilic functional group.

In some embodiments, the ECL coreactant is an amine having a structure $NR^1R^2R^3$, wherein $R^1$, $R^2$ and $R^3$ are $C_{1-10}$ aliphatic groups wherein at least one of the $C_{1-10}$ aliphatic groups is substituted with at least one hydrophilic functional group. In some embodiments, the hydrophilic functional group is a charged group, for example, a negatively charged group. Hydrophilic functional groups can be hydroxyl, hydroxycarbonyl, amino, aminocarbonyl, amidine, imino, cyano, nitro, nitrate, sulfate, sulfonate, phosphate, phosphonate, silicate, carboxylate, borate (B(OH)$_3$), guanidinium, carbamide, carbamate, carbonate, sulfamide, silyl, siloxy, and amide.

In some embodiments, the ECL coreactant has the structure (n-propyl)$_2$N(CH$_2$)$_{n1}$R*: wherein n1 is an integer from 1 to 10; and R* is a hydrophilic functional group, as defined above. In some embodiments, n1 is 2. In some embodiments, n1 is 3. In some embodiments, n1 is 4.

In some embodiments, the ECL coreactant has the formula

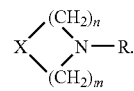

wherein X is selected from —(CH$_2$)—, —(CHR$^{11}$)—, —(CR$^{11}$R$^{12}$)—, a heteroatom, and —N(R$^{11}$)—; R is a C$_{1-10}$ aliphatic group substituted with at least one hydrophilic functional group; each of R$^{11}$ and R$^{12}$ is independently a C$_{1-10}$ aliphatic group optionally substituted with at least one hydrophilic functional group; and n and m are independently integers from 1 to 10.

In some embodiments, the heteroatom can be, for example, —O— or —S—.

In some embodiments, n is 2. In some embodiments, n is 3. In some embodiments, n is 4. In some embodiments, m is 2. In some embodiments, m is 3. In some embodiments, m is 4.

In some embodiments, $R^{11}$ is a $C_{1-4}$ aliphatic group.

In some embodiments, R is a $C_{1-4}$ aliphatic group substituted with at least one hydrophilic functional group.

When X is —N($R^{11}$)—, $R^{11}$ can be, for example, —(CH2)$_{n3}$—$R^{13}$, wherein n3 is an integer from 3 to 20, or, for example, from 3 to 10, and $R^{13}$ is H, an aliphatic group, or a hydrophilic functional group. In some embodiments n3 is 3. In some embodiments n3 is 4.

In some embodiments, R is —(CH$_2$)$_{n2}$—$R^{12}$, wherein n2 is an integer from 3 to 20, for example 3 to 10.

In some embodiments n2 is 3. In some embodiments n2 is 4. In some embodiments n2 is 5.

In some embodiments, $R^{12}$ is a hydrophilic functional group. In some embodiments $R^{12}$ is a carboxylate or sulfonate.

The use of ECL coreactants having hydrophilic functional groups (and, in particular, ECL coreactants that are zwitterionic at neutral pH) has a variety of advantages that are unrelated to their ability to act as ECL coreactants. These species tend to be highly water soluble and to have low vapor pressure. For these reasons it is possible to produce highly concentrated stock solutions that may be diluted as necessary for use. It is also possible to prepare dried reagents comprising the ECL coreactants without uncertainty due to loss of ECL coreactant in the vapor phase. Furthermore, when present in a dry composition, these ECL coreactants resolubilize quickly in a minimum of volume.

ECL coreactants include, but are not limited to, lincomycin; clindamycin-2-phosphate; erythromycin; 1-methylpyrrolidone; diphenidol; atropine; trazodone; hydroflumethiazide; hydrochlorothiazide; clindamycin; tetracycline; streptomycin; gentamicin; reserpine; trimethylamine; tri-n-butylphosphine; piperidine; N,N-dimethylaniline; pheniramine; bromopheniramine; chlorpheniramine; diphenylhydramine; 2-dimethylaminopyridine; pyrilamine; 2-benzylaminopyridine; leucine; valine; glutamic acid; phenylalanine; alanine; arginine; histidine; cysteine; tryptophan; tyrosine; hydroxyproline; asparagine; methionine; threonine; serine; cyclothiazide; trichlormethiazide; 1,3-diaminopropane; piperazine, chlorothiazide; barbituric acid; persulfate; penicillin; 1-piperidinyl ethanol; 1,4-diaminobutane; 1,5-diaminopentane; 1,6-diaminohexane; ethylenediamine; benzenesulfonamide; tetramethylsulfone; ethylamine; n-hexylamine; hydrazine sulfate; glucose; n-methylacetamide; phosphonoacetic acid; and/or salts thereof.

ECL coreactants include, but are not limited to, 1-ethylpiperidine; 2,2-Bis(hydroxymethyl)-2,2',2"-nitrilotriethanol (BIS-TRIS); 1,3-bis[tris(hydroxymethyl)methylamino]propane (bis-Tris propane) (BIS-TRIS propane); 2-Morpholinoethanesulfonic acid (MES); 3-(N-Morpholino)propanesulfonic acid (MOPS); 3-Morpholino-2-hydroxypropanesulfonic acid (MOPSO); 4-(2-Hydroxyethyl)piperazine-1-(2-hydroxypropanesulfonic acid) (HEPPSO); 4-(2-Hydroxyethyl)piperazine-1-propanesulfonic acid (EPPS); 4-(N-Morpholino)butanesulfonic acid (MOBS); N,N-Bis(2-hydroxyethyl)glycine (BICINE); DAB-AM-16, Polypropylenimine hexadecaamine Dendrimer (DAB-AM-16); DAB-AM-32, Polypropylenimine dotriacontaamine Dendrimer (DAB-AM-32); DAB-AM-4, Polypropylenimine tetraamine Dendrimer (DAB-AM-4); DAB-AM-64, Polypropylenimine tetrahexacontaamine Dendrimer; DAB-AM-8, Polypropylenimine octaamine Dendrimer (DAB-AM-8); di-ethylamine; dihydronicotinamide adenine dinucleotide (NADH); di-iso-butylamine; di-isopropylamine; di-n-butylamine; di-n-pentylamine; di-n-propylamine; di-n-propylamine; ethylenediamine tetraacetic acid (EDTA); Glycyl-glycine (Gly-Gly); N-(2-Acetamido) iminodiacetic acid (ADA); N-(2-Hydroxyethyl)piperazine-N'-(2-ethanesulfonic acid) (HEPES); N-(2-Hydroxyethyl) piperazine-N'-(4-butanesulfonic acid) (HEPBS); N,N-Bis(2-hydroxyethyl)-3-amino-2-hydroxypropanesulfonic acid (DIPSO); N,N-Bis(2-hydroxyethyl)taurine (BES); N-ethylmorpholine; oxalic acid; Piperazine-1,4-bis(2-hydroxypropanesulfonic acid) (POPSO); s-butylamine; sparteine; t-butylamine; triethanolamine; tri-ethylamine; tri-iso-butylamine; tri-iso-propylamine; tri-n-butylamine; tri-n-butylamine; tri-n-pentylamine; N,N,N',N'-Tetrapropyl-1,3-diaminopropane; oxalate; peroxodisulfate; piperazine-1,4-bis(2-ethanesulfonic acid) (PIPES); tri-n-propylamine; 3-dimethylamino-1-propanol; 3-dimethylamino-2-propanol; 1,3-Bis(dimethylamino)-2-propanol; 1,3-Bis(diethylamino)-2-propanol; 1,3-Bis(dipropylamino)-2-propanol; N-tris(hydroxymethyl) methyl-2-aminoethane sulfonic acid (TES); piperazine-N,N'-bis-3-propanesulfonic acid (PIPPS); piperazine-N,N'-bis-4-butanesulfonic acid (PIPBS); 1,6-diaminohexane-N,N,N',N'-tetraacetic acid; 4-(di-n-propylamino)-butanesulfonic acid; 4-[bis-(2-hydroxyethane)-amino]-butanesulfonic acid; azepane-N-(3-propanesulfonic acid); N,N-bis propyl-N-4-aminobutanesulfonic acid; piperazine-N,N'-bis-3-methyl-propanoate; piperazine-N-2-hydroxyethane-N'-3-methyl-propanoate; piperidine-N-(3-propanesulfonic acid); piperidine-N-(3-propionic acid) (PPA); 3-(di-n-propylamino)-propanesulfonic acid; and/or salts thereof.

In some embodiments, the ECL coreactant is selected from piperazine-1,4-bis(2-ethanesulfonic acid) (PIPES), tri-n-propylamine, N,N,N',N'-Tetrapropyl-1,3-diaminopropane, 1,3-Bis(dipropylamino)-2-propanol, and salts and mixtures thereof.

In some embodiments, the ECL coreactant is selected from oxalate or tri-n-propylamine.

D. Electrochemical Cells and Electrodes

The term "half-cell" refers to half of an electrolytic or voltaic cell, where either oxidation or reduction occurs.

The term "half-cell reaction" refers the reaction that occurs when electrons are exchanged between an electrode in the half-cell and the electrolyte. At the anode the half-cell reaction is oxidation, while the half-cell reaction at the cathode is reduction.

The term "half-cell product" refers the products formed from a half-cell reaction.

The term "working electrode" refers to the test or specimen electrode in an electrochemical cell where one half-cell reaction takes place. In the present instance the working electrode is also a faradaic electrode.

The term "counter electrode" refers to an electrode in an electrochemical cell to which charge flows, which charge is necessarily of an opposite sign to that charge that flows to the working electrode. In some embodiments the counter electrode is also a capacitive electrode.

The term "reference electrode" refers to a nonpolarizable electrode with a known and highly reproducible potential used for potentiometric and voltammetric analyses. The reference electrode provides a stable reference point, against which the voltage of a working electrode is measured. Typical reference electrodes are the silver/silver chloride electrode and the calomel electrode. High stability of the potential of the reference electrode is achieved by employing an oxidation-reduction system where all participants (usually two, an oxidant and reductant) of the reaction are present at high concentrations. During use no significant current is passed so as to alter the concentration of oxidant or reductant. A reference electrode (RE) differs from a faradaic electrode.

The term "faradaic electrode" refers to an electrode that generally obeys Faraday's law while being used in an electrochemical cell. Faradaic electrodes exclude reference electrodes. A faradaic electrode allows significant current to pass which can alter the concentration some or all of the oxidation-reduction participants. For example, a faradaic electrode may operate on a system where only the oxidant is initially present so as to form a reductant. For example, a faradaic electrode may operate on a system where only the reductant is initially present so as to form a oxidant.

Faradaic electrodes can be made from metals and semiconductors, such as platinum sheet electrodes, platinum wire electrodes, platinum alloy electrodes (including alloying elements Ni, Pd, Au, Co, Fe, Ru, Os, Cr, Mo, Zr, Nb, Ir, Rh, and W), iridium electrodes, iridium alloy electrodes (including alloying elements Ni, Pd, Co, Fe, Ru, Os, Cr, Mo, Zr, Nb, Pt, Rh, and W), rhodium electrodes, rhodium alloy electrodes (including alloying elements Au, Ni, Pd, Co, Fe, Ru, Os, Cr, Mo, Zr, Nb, Ir, Pt, and W), glassy carbon electrodes, graphite electrodes, carbon electrodes, carbon ink electrodes, gold electrodes, silver electrodes, silver alloy electrodes, nickel electrodes, nickel alloy electrodes, stainless steel working electrodes, and the like. See, for example, Bard and Faulkner; Wiley, *Electrochemical Methods: Fundamentals and Applications: 2 ed* (2000).

In some embodiments of the present invention, the faradaic working electrode comprises carbon, gold, gold alloys, platinum, platinum alloys, iridium, iridium alloys, silver, sliver alloys, nickel, nickel alloys, stainless steel, or mercury.

In some embodiments, the faradaic working electrode is an ultramicroelectrode.

The term "capacitive electrode" refers to an electrode that has limited electron transfer to the electrolyte solution. The capacitive electrode is characterized by an ability to build up or trap charge within the electrode. The charge trapped within the electrode is stabilized by the build-up or collection of ionic species (a so-called double layer) in the electrolyte at the electrode surface/electrolyte interface. An electrode may be considered to be a capacitive electrode even if some galvanic current is measurable.

One method to characterize a capacitive electrode is via the amount of galvanic current per unit area that can pass through the electrode. This current is sometimes referred to as a "leakage current density". For the sake of clarity, the leakage current is measured using the following method. 1. Use a cell containing (a) the test electrode with geometric area of 0.1 $cm^2$, (b) a silver/silver chloride reference electrode whose electrochemical area is at least 10 times the test electrode area and wherein the separation between the electrodes is less than the largest dimension of the reference electrode, and (c) an inert supporting electrolyte: aqueous 3 M KCl, pH 6 to 8 (adjusted with HCl or KOH). Apply voltage that steps from the rest potential (the potential at which no current flows) to the rest potential plus 0.32 V. Measure the current as a function of time. The experiment-1-time-constant is the absolute value of the ratio of the current and the slope at the time at which the slope of the current decay is greatest. 2. Using same cell from step 1, add ferricyanide and ferrocyanide such that final concentration of each is 1 mM, provide sufficient solution stirring such that the stirred cell has a mass transfer coefficient of $10^{-2}$ cm/s, use a total solution volume such that the volume is greater than or equal to the test electrode area multiplied by mass transfer coefficient multiplied by experiment-1-time-constant multiplied by 100, then apply same voltage waveform as step 1. The "leakage current" is defined as the current measured in this second step after 25 experiment-1-time-constants. The leakage current density is the defined as the leakage current divided by the test electrode area.

In some embodiments, a capacitive electrode is one whose leakage current density is less than 10 $\mu A/cm^2$. In some embodiments, a capacitive electrode is one whose leakage current density is less than 1 $\mu A/cm^2$. In some embodiments, a capacitive electrode is one whose leakage current density is less than 100 $nA/cm^2$. In some embodiments, a capacitive electrode is one whose leakage current density is less than 10 $nA/cm^2$. In some embodiments, a capacitive electrode is one whose leakage current density is less than 1 $nA/cm^2$. In some embodiments, a capacitive electrode is one whose leakage current density is less than 100 $pA/cm^2$. In some embodiments, a capacitive electrode is one whose leakage current density is from about 100 $pA/cm^2$ to about 10 $\mu A/cm^2$. In some embodiments, a capacitive electrode is one whose leakage current density is from about 1 $nA/cm^2$ to about 1 $\mu A/cm^2$ One method to characterize a capacitive electrode is via the electrode's time constant. The time constant is defined as the product of the electrode resistance and electrode capacitance. The following apparatus is used to measure these quantities (which is intended to minimize the impedance of the solution and a non-test electrode in order to better ascertain the properties of a test electrode): (1) a cell containing the test electrode and an Ag/AgCl electrode whose electrochemical area is at least 10 times the area of the test electrode wherein the separation between the electrodes is less than the largest dimension of the reference electrode; (2) an aqueous solution in the cell consisting essentially of 760 $\mu M$ $K_4Fe(CN)_6$, 760 $\mu M$ $K_3Fe(CN)_6$, and 1 M KCl, pH 6-8 (adjusted with KOH and/or HCl); and (3) a voltage generator that applies a DC bias voltage equal to the rest potential (the potential at which the current is 0) plus a 59 mV peak sinusoid and a current meter. A swept sine technique is used to measure the frequency dependence of the complex impedance (applied voltage divided by measured current). Let z1 equal the asymptotic value of the magnitude of the complex impedance as the frequency approaches 0. Let z2 equal the asymptotic value of the magnitude of the complex impedance in the high frequency limit. Let $\omega_{min}$ equal the radian frequency at which the phase angle of the complex impedance is the most negative. The electrode resistance equals z1−z2. The electrode capacitance equals $$\frac{\sqrt{z1/z2}}{(z1-z2)\omega_{min}}.$$

In some embodiments, a capacitive electrode is one whose time constant is greater than or equal to 1 second. In some embodiments, a capacitive electrode is one whose time constant is greater than or equal to 10 seconds. In some embodiments, a capacitive electrode is one whose time constant is greater than or equal to 100 seconds. In some embodiments, a capacitive electrode is one whose time constant is greater than or equal to 1,000 seconds. In some embodiments, a capacitive electrode is one whose time constant is greater than or equal to 10,000 seconds. In some embodiments, a capacitive electrode is one whose time constant is from about 1 second to about 100,000 seconds. In some embodiments, a capacitive electrode is one whose time constant is from about 5 seconds to about 10,000 seconds. In some embodiments, a capacitive electrode is one whose time constant is from about 10 seconds to about 1,000 seconds. In some embodiments, a capacitive electrode is one whose time constant is from about 10 seconds to about 100 seconds.

One method to characterize a capacitive electrode is by the ratio of the time constants of the capacitive electrode and the working electrode. This ratio is related to the ratio of the amount of electrochemical product generated at the two electrodes. Typically, as the time constant of the capacitive electrode increases relative to the working electrode, the amount of electrochemical product generated at the capacitive electrode relative to the working electrode decreases. In this definition, a capacitive electrode cannot be defined in isolation; rather it is defined relative to a particular working electrode. To compute the ratio of the time constants of the capacitive electrode and the working electrode, each time constant is measured individually using the method described in the previous paragraph. In some embodiments, a capacitive electrode is one whose time constant is 10 times larger than the time constant of the working electrode. In some embodiments, a capacitive electrode is one whose time constant is 100 times larger than the time constant of the working electrode. In some embodiments, a capacitive electrode is one whose time constant is 1,000 times larger than the time constant of the working electrode. In some embodiments, a capacitive electrode is one whose time constant is 10,000 times larger than the time constant of the working electrode.

In some embodiments, the capacitive counter electrode is an ideally polarized electrode.

In some embodiments, the capacitive counter electrode comprises a semiconductive material with an oxide layer.

In some embodiments, the capacitive counter electrode comprises a conductive material with an oxide layer.

In some embodiments, the capacitive counter electrode comprises a material whose bulk resistivity is less than about $10^{-2}$ Ωm at 20° C., covered by an electrically insulating material having a bulk resistivity greater than $10^4$ Ωm at 20° C. wherein the insulating material has a mean thickness that is less than about 1 μm.

In some embodiments, the insulating material has a bulk resistivity greater than $10^5$ Ωm at about 20° C. and the insulating material has a mean thickness that is less than about 100 nm.

In some embodiments, the capacitive counter electrode comprises oxides of silicon, titanium, aluminum, magnesium, zirconium, and/or tantalum.

The term "electrolyte" refers to a medium that provides the ion transport mechanism between the electrodes of an electrochemical cell. Generally electrolytes are substances that dissociates into ions when in solution and are capable of conducting electricity, such as acids, bases, and salts.

The term "capacitance" refers to that property which permits the storage of electrically separated charges when potential differences exist between conductors. The capacitance of a two-terminal capacitor is defined as the ratio between the electric charge ohmically connected to one terminal and the resultant difference in potential between the terminals. In the present invention the capacitive electrode acts like a capacitor when it stores charge within the electrode and collects counter charges at the electrode electrolyte interface.

The term "permittivity" equals to the electric flux density (D) divided by the electric field strength (E). The permittivity of a material can change with frequency. In these electro-chemical applications, the relevant frequency range is low, with the upper end rarely exceeding 10's of kHz. The capacitance of a parallel plate capacitor is approximately equal to the permittivity of the material between the plates multiplied by the area of one of the plates divided by distance between the plates.

"Coulometric methods" are known in the art and can be used to quantitatively add electrons to or remove electrons from a system. Coulometric methods involve electrochemical generation of chemical species in a solution via an electrode reaction. The amount of product ($N_o$) generated at the faradaic working electrode can be controlled by the charge passed at that electrode, as governed by Faraday's law:

$$N_o = q/(nF)$$

where q is the charge passing through the electrode, n is the number of electrons used to generate 1 molecule of product at the working electrode, and F is Faraday's constant. When using coulometric methods, care must be taken to account for the electrode's capacitance.

Capacitive electrodes can be made from oxidized metals and semiconductors. Further examples of capacitive electrodes include electrodes made from materials having a bulk resistivity less than $10^{-2}$ Ω/m at 20° C., covered by a thin (mean thickness less than 10 μm) insulating material, including dielectrics for integrated circuit fabrication such as silicon dioxide, silicon nitride, TiN, TaN, TiAlN, TaAlN, TaSiN, $SrTiO_3$, $Ta_2O_5$, $TiO_2$, $Y_2O_3$, $ZrO_2$, $HfO_2$, $Al_2O_3$, $BaSrTiO_3$, FOx®-1x and FOx®-2x (Dow Corning, Midland, Mich.) flowable oxide product families (comprising hydrogen silsesquioxane); solder masks (as described in the standard IPC-SM-840C: Qualification and performance of permanent solder mask); and conformal coatings (as described in the stand IPC-SM-840 Qualification and Performance of Permanent Solder Mask) such as parylene and Novec™ EGC-1700, EGC-1702, EGC-1704, and EGC-1720 electronic coatings (3M, MN).

Further examples of capacitive electrodes include electrodes made from materials having a bulk resistivity less than $10^{-2}$ Ωm at 20° C., covered by a thin (mean thickness less than 1 μm) insulating material such as oxides of silicon, titanium, aluminum, magnesium, zirconium, and/or tantalum.

Further examples of capacitive electrodes include electrodes made from materials having a bulk resistivity less than $10^{-2}$ Ωm at 20° C., covered by a thin (mean thickness less than 1 μm) insulating material deposited by chemical vapor deposition or by spin coating.

Further examples of capacitive electrodes include electrodes made from materials having a bulk resistivity less than $10^{-2}$ Ωm at 20° C., covered by a thin (mean thickness less than 1 βm) insulating material having a bulk resistivity greater than $10^4$ Ωm at 20° C. Thinner insulating layers can provide increased capacitance for a given electrode area; however, thinner insulating layers may cause increased leakage currents through the presence of pin-holes in the insulation or by dielectric breakdown. In some embodiments, the mean thickness of the insulating layer on the capacitive electrode is less than 10 μm. In some embodiments, the mean thickness of the insulating layer on the capacitive electrode is less than 1 μm. In some embodiments, the mean thickness of the insulating layer on the capacitive electrode is less than 100 nm. In some embodiments, the mean thickness of the insulating layer on the capacitive electrode is less than 10 nm. In some embodiments, the mean thickness of the insulating layer on the capacitive electrode is less than 1 nm. In some embodiments, the mean thickness of the insulating layer on the capacitive electrode is from about 1 nm to about 10 μm. In some embodiments, the mean thickness of the insulating layer on the capacitive electrode is from about 10 nm to about 1 µm. In some embodiments, the mean thickness of the insulating layer on the capacitive electrode is from about 10 nm to about 100 nm.

The capacitance of a capacitive electrode increases with the permittivity of the insulating layer. In some embodiments, the insulating layer has a permittivity that is about equal to the permittivity of free space. In some embodiments, the insulating layer has a permittivity that is greater than about 1 times and less than about 3 times the permittivity of free space. In some embodiments, the insulating layer has a permittivity that is greater than about 3 times and less than about 5 times the permittivity of free space. In some embodiments, the insulating layer has a permittivity that is greater than about 5 times and less than about 10 times the permittivity of free space. In some embodiments, the insulating layer has a permittivity that is greater than about 10 times and less than about 100 times the permittivity of free space. In some embodiments, the insulating layer has a permittivity that is greater than about 100 times the permittivity of free space.

II. Certain Embodiments of the Cell and Electrodes

The present invention is directed to methods and apparatus utilizing an electrochemical cell comprising a faradaic working electrode and a capacitive counter electrode. The capacitive counter electrode can be characterized by, for example, its leakage current density, its time constant, and the ratio of its time constant to the working electrode's time constant, or combinations thereof. In some embodiments the electrochemical apparatus is operated in a manner that allows a constant faradaic current at the working electrode while producing little to no oxidation or reduction products at the counter electrode. In some embodiments the electrochemical apparatus is operated in a manner that allows a constant faradaic current at the working electrode while reducing the amount of oxidation or reduction products at the counter electrode.

Typical electrochemical cells employ faradaic electrodes at both the anode (where oxidations occur) and the cathode (where reductions occur). A separate half-reaction occurs at each of these electrodes, producing a different product (half-cell product) at each of the electrodes. The solution as a whole maintains charge (ionic) neutrality at all times because equal charges of anionic and cationic species are generated by each of the half-cell reactions at the corresponding electrodes. Generally only the reaction or product at the working electrode is of interest. In fact, the counter electrode is often placed in a different compartment, separated by an ionically conducting "cell-separator" to prevent mixing of the half-cell products formed at each of the electrodes. Salt bridges and other ionically conducting cell-separators are known in the art. See, for example, Bard and Faulkner; Wiley, *Electrochemical Methods: Fundamentals and Applications:* 2 ed (2000).

The present invention can be used in many sizes of electrochemical cells that comprise a faradaic working electrode and a capacitive counter electrode. Exemplary size ranges for the faradaic working electrode include macroscopic geometrical areas of about 0.1 µm$^2$ to about 10 m$^2$, about 10 µm$^2$ to about 10000 cm$^2$, about 10 µm$^2$ to about 100 cm$^2$, about 10000 µm$^2$ to about 10 cm$^2$, about 1 mm$^2$ to about 100 mm$^2$, and about 1 mm$^2$ to about 10 mm$^2$. Exemplary sizes for the faradaic working electrode include macroscopic geometrical areas of about 0.1 µm$^2$, 1 µm$^2$, 10 µm$^2$, 100 m$^2$, 1000 µm$^2$, 10000 µm$^2$, 1 mm$^2$, 10 mm$^2$, 100 mm$^2$, 1 cm$^2$, 10 cm$^2$, 100 cm$^2$, 1000 cm$^2$, 10000 cm$^2$, 1 m$^2$, or 10 m$^2$. Exemplary sizes and size ranges the capacitive counter electrode include those sizes for the faradaic working electrode plus larger sizes to accommodate such embodiments as electrode 202.

In some embodiments, the electrochemical cell can partially enclose a sample volume. For example, the cell can be a well in a multi-well assay plate, a beaker, a tube, a flow cell, or other shapes and sizes. In some embodiments, the faradaic and the capacitive counter electrode can be in a single cell, for example cell 200. In some embodiments, the counter electrode and the working electrode can be in individual cells conductively connected to one another by a salt bridge, frit, or other bridging means, which are well known in the art. The cell can also be configured so that only one of the faradaic working electrode and the counter electrode is positioned within the cell, and the other is positioned adjacent to the cell, but in contact with the fluid within the cell. In addition, the cell can be one of a plurality of single or split cells, for example, the wells of a multi-well plate or multiple tubes in an auto-sampling system.

The electrochemical cell can also be a flow cell. The flow cell can be configured with an inlet and outlet such that the fluids can flow through the inlet into the cell and then flow out of the cell through the outlet. Exemplary electrochemiluminescence flow cells and methods for their use are disclosed in U.S. Pat. No. 6,200,531.

In some embodiments, the electrochemical cell is capable of receiving an electrolyte solution. This solution can participate in electrochemical reactions at the faradaic working electrode when contacted by the faradaic working electrode and the capacitive counter electrode in the electrochemical cell and electrical energy is applied between the electrodes.

In some embodiments, the electrochemical cell can further comprise a reference electrode. In some embodiments, the cell does not comprise a reference electrode. The reference electrode, when present, can be used to better control the potential drop across the faradaic working electrode irrespective of the potential drop across the capacitive counter electrode until the voltage compliance limit of the potentiostat is attained or dielectric breakdown occurs at the capacitive counter electrode.

III. Certain Embodiments of the Apparatus

In some embodiments, the apparatus can comprise an assay-performance-substance comprising at least one of (a) a labeled binding partner for an analyte and (b) a labeled analog of the analyte. In some embodiments, the assay-performance-substance can be a dry composition. In some embodiments, the assay-performance-substance comprises an ECL moiety. In these embodiments, the apparatus may optionally comprise an ECL coreactant.

In some embodiments, the apparatus further comprises a vapor barrier that encloses the assays-performance-substance, for example, to prevent evaporation of a liquid composition or to prevent melt-back of a dry composition.

In some embodiments, the apparatus can comprise a filter in fluidic connection to the faradaic working electrode and capacitive counter electrode. Filtration is one method for removing interfering components of the sample matrix. The interfering components can be removed from the sample matrix prior to the sample entering the electrochemical cell. In this approach, the barrier of the filter can retain particulate components that might interfere with the detection process. Particulate components of the matrix can, for example, interfere with some of the detection methodologies that require capture or deposition of beads on a detection surface. Additionally, removing interfering components can decrease the amount of surface that is available to bind analyte. In some embodiments, the filter entrapped particulate components can be treated to release analyte for the detection process.

Filtration primarily separates components from solutions by presenting a physical barrier that can exclude particles larger than a given size. There are many different methods in the filtration art to make barriers of these types, each method a function of the base material being manipulated. For example, metal wire is commonly used to make woven screens that can be used to catch extremely large particles, for examples, particles over 50 microns in size. To capture smaller airborne particles, smaller diameter metal wire screens can be used, but they have limitations due to impedance to air flow (pressure drop). Polymer-based membranes are typically used to remove smaller particles from solutions. For example, the polymer nylon can be used in a phase inversion casting process to make membranes that range from about a 10 micron pore size rating, down to about a 0.1 micron pore size rating. Other polymer-based membranes (e.g. polyethersulphone, nitrocellulose, or cellulose acetate) can be made by a solvent evaporation casting process. The filtration medium is generally incorporated into a holding device that allows the fluid of interest to pass through the filter barrier in a controlled manner. In some embodiments, the invention can use a filter-containing filtration media using the polymer polyethersulphone (PES). In certain embodiments, the PES filter can be encased in a plastic housing that can be (a) attached to a syringe, (b) part of a single use disposable designed to ease robotic automation, or (c) part of a multiple-use disposable designed to filter a plurality of samples.

Filtration primarily separates components from solutions by size. In most filters, the pathway through the filter is not a straight hole, but rather a twisted path. This makes describing filter hole size somewhat operational in nature, and gives rise to the term "Pore Size Rating". In determining a filter's Pore Size Rating, filters are challenged with a known volume (or amount) of particles of a known size (known by a secondary means like microscopy, light scattering, or impedance measurements). Then, the amount of particles downstream of the filter is measured and compared to the amount of particles upstream of the filter, across multiple sizes of particles. When the ratio of downstream to upstream particles drops significantly below unity for a given size range of particles, the filter is said to have removal capacity for that size range. These ratios are typically described in logarithmic-based units of removal. For example, a filter rated at 5 microns will typically reduce the level of downstream particles greater than 5 microns by a ratio of 0.90 (90% removal or 1 log removal) to a ratio of 0.999 (99.9% removal: or 3 log removal). The pore size of the filter can be chosen based many factors. In some embodiments, the pore size can be large enough to pass the analyte, for example, anthrax spores, which are approximately 1 μm in size. In certain embodiments, the pore size can be small enough to block interfering components from the sample matrix. The pore size can also affect the rate of fluid flow across the filter, with smaller pores generally creating larger resistances to flow.

In some embodiments, the filter has a pore size rating of 5 microns. In some embodiments, the filter has a pore size rating of 0.1, 0.2, 0.5, 1, 2, 3, 4, 7, 10, 15, 20, 50, or 100 microns. In some embodiments, the filter has a pore size rating less than or equal to about 100 microns and greater than or equal to about 10 microns. In some embodiments, the filter has a pore size rating less than or equal to about 10 microns and greater than or equal to about 1 microns. In some embodiments, the filter has a pore size rating less than or equal to about 1 microns and greater than or equal to about 0.1 microns. In some embodiments, the filter has a pore size rating less than or equal to about 0.1 microns and greater than or equal to about 0.02 microns.

In some embodiments, the apparatus comprises (a) an electrochemical cell comprising a faradaic working electrode and a capacitive counter electrode wherein the electrochemical cell is capable of receiving an electrolyte solution; and (b) any combination of the reference electrode, an assay-performance-substance comprising at least one of (i) a labeled binding partner for an analyte and (ii) a labeled analog of the analyte, the ECL coreactant, and the filter. In certain embodiments, the apparatus is an expendable or replaceable element in a larger instrument, for example, to prevent the larger instrument from contacting the electrolyte solution (which may contain a sample comprising an analyte that is desired to be detected). In certain of these embodiments, the apparatus comprises the assay-performance-substance in a dry composition and a vapor barrier that encloses the assay-performance-substance.

In some embodiments, the apparatus comprises any of the above embodiments (for example, an apparatus comprising an electrochemical cell comprising a faradaic working electrode and a capacitive counter electrode wherein the electrochemical cell is capable of receiving an electrolyte solution that can simultaneously contact said faradaic working electrode and said capacitive counter electrode), plus a source of electrical energy capable of being electrically connectable to the faradaic working electrode and the capacitive counter electrode. Consistent with the principles of the invention, there are many possible sources of electrical energy. The electrical energy applied to the electrochemical cell can be generated using conventional instrumentation such as potentiostats, galvanostats, and/or similar instruments. In some embodiments, a voltage source, a current source, a source of charge, and/or a power source can be used with either a constant or a time-varying waveform comprising offsets, steps, ramps, sinusoids, and combinations thereof. In some embodiments, a third electrode can be used as a feedback mechanism to control the voltage across the faradaic working electrode. In some embodiments, the energy can come from a local energy store, such as a battery, super-capacitor, flywheel, and/or a hydrocarbon source (e.g., gasoline and/or methane). In some embodiments, a photovoltaic device can provide the energy. In some embodiments, power from the AC network can be used. In some embodiments, semiconductor devices can use the energy store to control charge, voltage, and/or current applied to the electrodes over time. In some embodiments, a computing device (e.g., a microprocessor, microcontroller, or computer) is used to control the application of electrical energy to the electrochemical cell.

In some embodiments, the apparatus comprises any of the above embodiments (for example, an apparatus comprising 1. an electrochemical cell comprising a faradaic working electrode and a capacitive counter electrode wherein the electrochemical cell is capable of receiving an electrolyte solution that can simultaneously contact said faradaic working electrode and said capacitive counter electrode and 2. a source of electrical energy capable of being electrically connectable to the faradaic working electrode and the capacitive counter electrode), plus a magnet located so as to be able to exert a magnetic force on magnetizable particles located at the faradaic working electrode.

In some embodiments, the magnet can be reversibly moved from its position beneath the faradaic electrode to reduce the magnetic force applied on magnetizable beads in the sample by the magnet.

In some embodiments, the magnet can comprise either a permanent magnet or an electromagnet.

In some embodiments, the magnet can comprise a dipole magnet, a sandwich magnet, or a channel magnet.

In some embodiments, the apparatus comprises any of the above embodiments (for example, an apparatus comprising 1. an electrochemical cell comprising a faradaic working electrode and a capacitive counter electrode wherein the electrochemical cell is capable of receiving an electrolyte solution that can simultaneously contact said faradaic working electrode and said capacitive counter electrode and 2. a source of electrical energy capable of being electrically connectable to the faradaic working electrode and the capacitive counter electrode), plus a photodetector positioned to detect light emitted on the faradaic working electrode. In some embodiments, the photodetector can be a photomultiplier tube, photodiode, CMOS device, or a charge-coupled device.

In some embodiments, the apparatus comprises any of the above embodiments (for example, an apparatus comprising 1. an electrochemical cell comprising a faradaic working electrode and a capacitive counter electrode wherein the electrochemical cell is capable of receiving an electrolyte solution that can simultaneously contact said faradaic working electrode and said capacitive counter electrode and 2. a source of electrical energy capable of being electrically connectable to the faradaic working electrode and the capacitive counter electrode), plus a pump arranged to be able to move liquid across or onto the faradaic working electrode. In some embodiments, the pump can be modeled as a pressure source (e.g., an impeller pump, one that uses gravity, or a pump based on capillary action), or as a volume velocity source (e.g., a peristaltic pump, syringe pump, gear pump, or positive displacement pump). In some embodiments, the pump moves liquid across the faradaic working electrode. In some embodiments, the pump is arranged to be able to move liquid across or onto the faradaic working electrode by using positive gauge pressures. In some embodiments, the pump is arranged to be able to move liquid across or onto the faradaic working electrode by using negative gauge pressures. In some embodiments comprising a filter, the pump can be used to remove filtrate from the filter; for example, fluid can be moved through the filter by gravity flow or by pressure, in which positive gauge pressure is applied upstream of the filter or negative gauge pressure (vacuum) is applied downstream of the filter. This filtrate can, for example, be dispensed into the electrochemical cell and onto the faradaic working electrode. In some embodiments comprising a flow cell, the pump can be used to transport fluids into and out of the flow cell.

The electrochemical cell can be used in conjunction with various automation systems such as an automatic drive mechanism or an alignment device to cause relative motion between the cell and the electrodes. An exemplary apparatus that comprises a flow-cell comprising a flow cell comprising capacitive counter electrode and a faradaic working electrode can further comprise a pump for aspirating and/or dispensing fluids into and out of the flow cell and an electrical energy source to drive the electrodes. In some embodiments, the exemplary apparatus can further comprise a fluid handling station for introducing one or more reagents and/or one or more samples that can include gases and liquids. The fluid handling station can comprise flow control valves as well as a manifold for accepting pipettor for aspirating/dispensing fluids from one or more locations into the cell. Additional flow control valves can also be present, as well as reagent/gas detectors.

When a potential is applied to an electrochemical cell with a faradaic working electrode and a capacitive counter electrode, electrons cross the faradaic electrode interface and a charge builds up in the capacitive electrode. The charge build-up in the counter electrode can be described by the equation for a capacitor in an electrical circuit: $q/V=C$, where q is the charge on the capacitor (in coulombs), V is the potential across the capacitor (in volts) and C is the capacitance (in Farads). The capacitance of an electrode may change as a function of the potential applied to the system; for example, the distance between the double layer and the electrode may increase as the amount of charge in the double layer increases. To a good approximation, the capacitive capability of an electrode is proportional to the surface area exposed to the solution. This electrochemical surface area can be larger than the macroscopic geometrical surface area by roughening the surface. The ratio of the electrochemical surface area to the macroscopic geometrical surface area can be, for example, from about 1 to about 1000, or from about 1 to about 10, or from about 10 to about 100, or from about 100 to about 1000. The ratio of the electrochemical surface area to the macroscopic geometrical surface area can be, for example, greater than or equal to about 1, about 2, about 3, about 5, about 10, about 30, about 100, about 300 or about 1,000. Methods to increase the roughness and thereby increase the electrochemical surface area include mechanical abrasion (e.g., through the use of sandpaper and/or sand blasting), plasma etching, ion and/or electron beam irradiation, depositing a rough coating (e.g., using techniques such as thermal spray, plating, or electrodeposition, ink-jet, sputtering, chemical vapor deposition), chemical etching, laser ablation, and electrochemical surface modification. Other methods to obtain a large roughness include using a highly rough starting material as the electrode, for example, sintered particles, platinum black, carbon nanotubes and carbon black inks. To efficiently add to the electrochemical surface area, the characteristic dimension of the roughness is preferably larger than (but not required to be) about 1 nm so that ions can easily contact all of the area.

Figure 2:
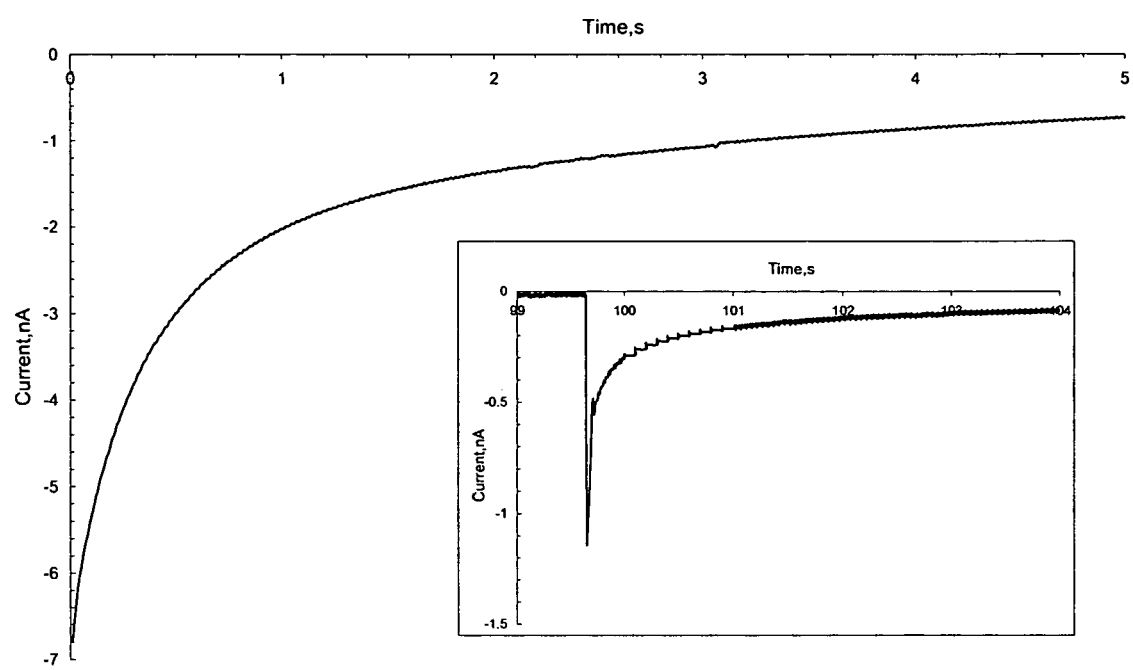
FIG. 2. Charging current as a function of time in a system of Pt/water/$SiO_2$/Si under a bias of 1 V applied between Pt and Si. After the charging current reached baseline, the circuit was disconnected for about 8 s and reconnected again still under the same bias; only a very small charging current was seen as shown in the inset.

When employing a voltage source to drive a capacitive counter electrode and a faradaic working electrode, the current decreases with time as charge is trapped in the counter electrode (See FIG. 2). One might expect that the amount of current at the working electrode is limited by the amount of charge that can be contained in the counter electrode at the applied voltage during operation of the electrochemical cell, which is determined by the capacitance of the electrode; however, this invention contemplates several methods of generating additional current, if additional current is desired.

In some embodiments, the apparatus comprises any of the above embodiments, plus a mechanism to contact differing capacitive counter electrodes or differing areas of the same capacitive counter electrodes to an electrolyte solution that is contacting the faradaic working electrode. By exposing fresh parts of the counter electrode, the capacity increases thereby increasing the amount of current that can be driven through the working electrode. In some embodiments, the parts of the counter electrode that are charged can be unused for the remainder of the useful life of the cell. In some embodiments, the parts of the counter electrode that are charged can be discharged through contact with the air, through contact with another solution in a different cell, through the electrode's leakage current, or by reversing the direction of the current. By continuously exposing fresh parts of the counter electrode, faradaic currents at the working electrode can be mass-transport limited by the reactants at the working electrode.

Figure 6:
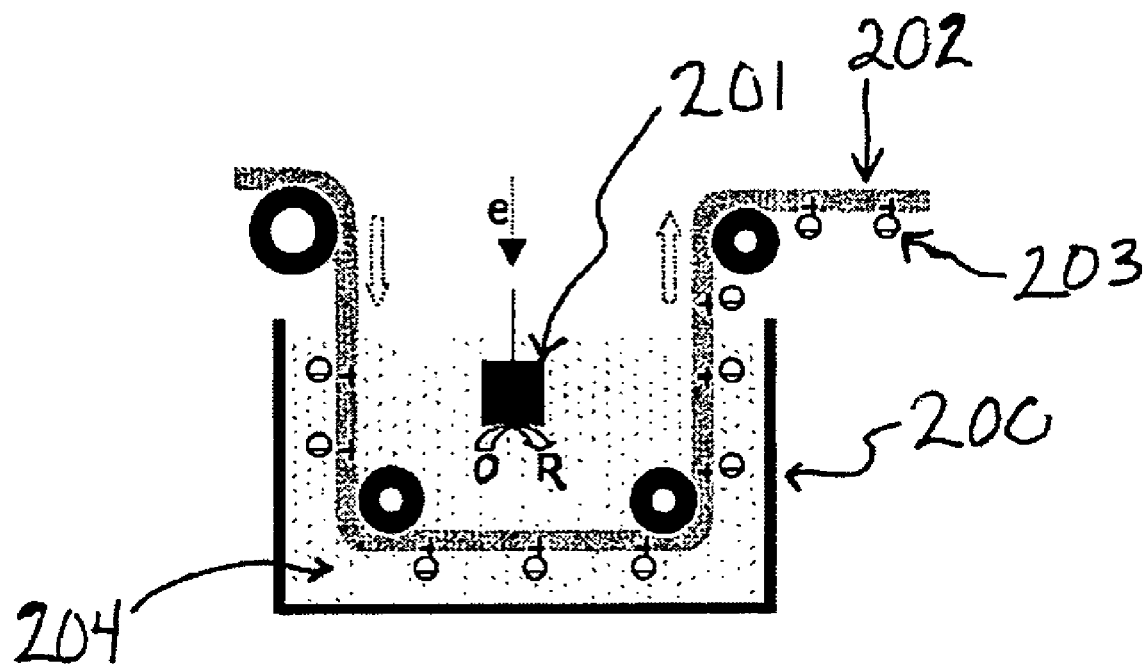
FIG. 6. Schematic diagram showing a motor driven, moving, blocked counter electrode, e.g. a conductive wire or tape coated with an insulating layer, through a solution containing an electrolyte under a bias to produce a continuous faradaic reaction at the working electrode.

FIG. 6 shows an exemplary embodiment of a cell whose counter electrode area exposed to the solution changes with time. The faradaic working electrode (201) can remain stationary in the cell while the capacitive counter electrode can be continuously moved through the electrolyte solution. For example, a conductive wire or film coated with a thin insulating layer (202) can be passed through the electrolyte (204) under a fixed bias as shown in FIG. 6. Anions (203) can be removed from the solution when a negative bias is applied to the metal electrode and excess cations can be left in the solution to provide electroneutrality for the cathodic faradaic reaction. Similarly, cations can be removed at the capacitive counter electrode when the working electrode is an anode. Alternatively, a streaming mercury electrode with a surface that is continuously renewed can be used if operated in the potential region where it behaves as an ideally polarized electrode. See, for details, I. M. Kolthoff, J. J. Lingane, *Polarograghy*, 2nd Ed, Vol. 1, Interscience Publishers, New York, p. 357, 1952. A Capacitive counter electrode can remove ions of a single polarity (i.e., without a counter ion) where the ionic charge can be compensated by electronic charge.

Exemplary combinations of the apparatus components described above include an electrochemical cell comprising: a faradaic working electrode; a capacitive counter electrode; and a source of electrical energy. In certain embodiments, the present invention is directed to an apparatus comprising an electrochemical cell comprising: a cell capable of receiving an electrolyte solution, a faradaic working electrode; and a capacitive counter electrode. In some embodiments, the cell is a flow cell.

Exemplary combinations of the apparatus components described above include an apparatus comprising an electrochemical cell used for performing a binding assay for an analyte in a sample based upon measurement of electrochemiluminescence at a faradaic working electrode surface, the electrochemical cell comprising: a cell for receiving a solution comprising (a) sample comprising the analyte and (b) a labeled binding partner for the analyte wherein the labeled binding partner comprises an ECL moiety; a faradaic working electrode having an electrode surface exposed to and positioned adjacent to a portion of the sample containing volume; a capacitive counter electrode having the electrode surface exposed to and positioned adjacent to a portion of the sample containing volume; a source of electrical energy sufficient to generate luminescence; a magnet for collecting beads along the faradaic working electrode surface; and a photodetector for measuring the amount of luminescence generated and, thereby, the quantity of analyte in the sample.

Exemplary combinations of the apparatus components described above include an apparatus comprising an electrochemical cell for use in analyzing a sample suspected of containing one or more analytes comprising: a filter fluidically connected to a sampling device; a pump arranged to be able to drive liquid flow across the filter; a cell for receiving a filtered sample suspected of containing one or more analytes; at least one faradaic working electrode; and at least one capacitive counter electrode; and means for measuring the quantity of analyte in the sample.

IV. Exemplary Methods

The invention also contemplates methods of use, for example, of apparatus embodiments described above. These methods of use include assay methods for determining the presence or amount of one or more analytes in a sample and methods of generating at least one electrochemical product at a working electrode while generating a discordantly smaller amount of electrochemical byproduct at a counter electrode.

In some embodiments, the method for determining the presence or amount of an analyte in a sample comprises the steps of contacting both a faradaic working electrode and a capacitive counter electrode with a solution comprising the sample and an electrolyte; supplying electrical energy between the faradaic working electrode and the capacitive counter electrode sufficient to provide for faradaic charge transfer at the faradaic working electrode; measuring at least one of (i) light, (ii) current, (iii) voltage, and (iv) charge to determine the presence or amount of the analyte in the sample.

In some embodiments, the method for determining the presence or amount of an analyte in a sample comprises the steps of
  (a) optionally preprocessing the sample;
  (b) contacting a faradaic working electrode to a solution comprising the optionally pre-processed sample; and an electrolyte;
  (c) contacting a capacitive counter electrode to the solution;
  (d) supplying electrical energy between the faradaic working electrode and the capacitive counter electrode sufficient to provide for faradaic charge transfer at the faradaic working electrode;
  (e) measuring at least one of (i) light, (ii) current, (iii) voltage, and (iv) charge to determine the presence or amount of the analyte in the sample.

Exemplary methods utilizing the measurement of light include luminescence assays, including fluorescence, chemiluminescence, and electrochemiluminescence assays. Exemplary methods utilizing the measurement of current include measuring the rate of generation of an electrochemical reactive species in the solution that is consumed by the faradaic working electrode. Exemplary methods utilizing the measurement of voltage include ion-selective electrodes. Exemplary methods utilizing the measurement of charge include measuring the capacitance of the capacitive counter electrode from which, for example, the concentration of the dominate ion and/or the Debye length of the solution can be estimated. Exemplary methods utilizing a combination of measurements include cyclic voltammograms involving measuring both current and voltage to examine, e.g., oxidization and reduction behavior in the solution. Various properties or combinations of properties of the physical measurements of light, current, voltage, and/or charge can be used to determine the quantity of analyte in the sample; for example, wavelength, frequency, energy, intensity, polarity, polarization, amplitude, waveform shape, and/or time dependency can be used.

In some embodiments, the solution used in the determination of the presence or amount of an analyte in a sample further comprises an ECL moiety, for example, those ECL moieties that comprise ruthenium or osmium. In some embodiments, the solution further comprises an ECL coreactant, for example, tertiary amines with and without hydrophilic functional groups, tertiary amines with alkyl groups optionally comprising hydrophilic functional groups, biological buffers with tertiary amines, and/or oxalate. In some embodiments, the electrical energy supplied between the faradaic working electrode and the capacitive counter electrode is sufficient to induce electrochemiluminesce and the quantity of analyte in the sample is determined by measuring luminescence. In some embodiments, the solution further comprises at least one of a labeled binding partner for an analyte and a labeled analog of the analyte. In some embodiments, the solution further comprises a second binding partner for the analyte wherein the second binding partner is linked to a support. In some embodiments, the support is a magnetizable bead.

In some embodiments, the method for determining the presence or amount of an analyte in a sample comprises the step of pre-processing the sample. Pre-processing can be, for example, filtering the sample through a filter to form a filtrate. Exemplary pore size ratings of the filter include those falling in the ranges of about 10 µm to about 100 µm, about 1 µm to about 10 µm, about 0.1 µm to about 1 µm, and about 0.02 µm to about 0.1 µm. Other pre-processing steps can be, for example, mixing the sample with a reagent whose pH is greater than 8 or less than 6 and an osmolarity is greater than or equal to 0.1 osmol/L. Other pre-processing steps can be, for example, mixing the sample with a reagent whose osmolarity is greater than or equal to 1.1 osmol/L.

In some embodiments, the assay methods can comprise the steps of inducing an ECL moiety in solution to emit light by applying an electrochemiluminescence-inducing electrical waveform to the working electrode in the presence of the ECL moiety; and measuring the luminescence emitted by the ECL moiety. In some embodiments, the assay methods can comprise the step of adding a second binding partner linked to a support (e.g., a magnetizable bead). In some embodiments using magnetizable beads, the method can comprise the steps of magnetically collecting the magnetizable beads along the faradaic working electrode surface through the use of a magnet (e.g., a permanent magnet or an electromagnet) that can optionally be reversibly removed from its location beneath the faradaic working electrode.

In some embodiments, the assay methods can employ a faradaic current flow through the faradaic working electrode that alternates in direction to reduce the potential across the capacitive counter electrode.

The present invention can be used for coulometric processes, for example, in micro and nanoscale electrochemical cells. In some embodiments, the present invention can be used to reduce the generation of an undesirable or destructive product at the counter electrode in an electrochemical cell. In some embodiments, the present invention can be used in electrochemiluminescent assays where the amount of an analyte in a sample can be determined by the amount of light generated at the working electrode, for example, in nanoscaled ECL assays where electrochemical products generated at the counter electrode have sufficient time to diffuse near the working electrode and may interfere with the assay.

The samples that can be analyzed using an electrochemical cell of the present invention can comprise at least one analyte. Measurement of an analyte in the sample can be carried out by any of the numerous techniques available in the art of biological assays, including but not limited to, nucleic acid hybridization assays, nucleic acid amplification assays, cell culture-based assays, agglutination tests, immunoassays (or other assay formats based on the use of specific binding partners of the marker of interest), immunochromatographic assays, enzymatic assays, etc. The detection method can be a binding assay, such as an immunoassay, and the detection can be performed by contacting an assay composition with one or more binding partners of the analyte. In certain embodiments, the assay uses a sandwich or competitive binding assay format. Examples of sandwich immunoassays performed on test strips are described by U.S. Pat. No. 4,168,146 to Grubb et al. and U.S. Pat. No. 4,366,241 to Tom et al. Examples of competitive immunoassay devices suitable for use with the present invention include those disclosed by U.S. Pat. No. 4,235,601 to Deutsch et al., U.S. Pat. No. 4,442,204 to Greenquist and U.S. Pat. No. 5,922,615 to Nowakowski et al. In certain embodiments, at least one of the binding partners employed in such an assay is immobilized on a support. In some embodiments, a labeled binding partner and/or a labeled analog of the analyte is used in the binding reactions. In some embodiments, the labeled binding partner comprises an ECL moiety.

A binding partner can be immobilized on the support by any conventional means, e.g., adsorption, absorption, noncovalent binding, covalent binding with a crosslinking agent, or covalent linkage resulting from chemical activation of either or both of the support or the binding partner. In some embodiments, the immobilization of the binding partner by the support can be accomplished using a binding pair. For example, one member of the binding pair, e.g., streptavidin or avidin, can be bound to the support and the other member of the same binding pair, e.g., biotin, can be bound to the first binding partner. Suitable means for immobilizing a binding partner on the support are disclosed, for example, in the Pierce Catalog, Pierce Chemical Company, P.O. Box 117, Rockford, Ill. 61105, 1994.

A. Certain Assay Methods

Binding assays can be carried out using magnetizable beads as a support for a solid phase binding assay using a flow cell-based design with permanent reusable flow cells, or single use replaceable cells. Complexes comprising an ECL moiety that are bound to magnetizable beads can be collected on an electrode in the flow cell with the aid of a magnet, for example, a dipole magnet, a sandwich magnet, a channel magnet and/or an electromagnet. The labels on the collected beads can be induced to emit ECL by application of a potential to the electrodes and the ECL can be measured to measure the amount of label. The ECL assay method can also comprise the step of introducing an ECL coreactant prior to application of the ECL-inducing potential.

In certain embodiments, a solid phase sandwich immunoassay can be run using the electrochemical cell of this invention. Two antibodies directed against the analyte are used: i) a capture antibody that is linked or capable of being linked (e.g., through the formation of a specific binding pair such as a biotin-streptavidin interaction) to a solid phase and ii) a detection antibody that is linked or capable of being linked (e.g., through the formation of a specific binding pair such as a biotin-streptavidin interaction) to a label, for example an ECL moiety. A sample comprising the solubilized analyte can be contacted with the two antibodies and the solid phase so that in the presence of the analyte the two antibodies can bind to the analyte to form a "sandwich complex" on the solid phase comprising the label. The label on the solid phase can be measured so as to measure the analyte in the sample.

The sample can be introduced into the cell as-collected or the sample can under go one or more preparations steps. See for example, THE IMMUNOASSAY HANDBOOK, $3^{rd}$ edition, David Wild editor, Elsevier, 2005.

In certain embodiments, the present invention can provide a method of detecting an analyte in a sample comprising the steps of: providing a cell for receiving an electrolyte solution and the sample which may comprise the analyte; placing the electrolyte solution in the cell; placing the sample in the cell; contacting a faradaic working electrode with the sample and electrolyte solution; contacting a capacitive counter electrode with the sample and electrolyte solution; supplying electrical energy to the electrodes sufficient to provide for faradaic charge transfer at the faradaic working electrode that can generate an electrochemical product; and determining the quantity of analyte in the sample.

In certain embodiments, the present invention can provide a method for determining the presence or amount of an analyte in a sample comprising the steps of (1) forming a solution comprising (a) the sample, (b) a labeled binding partner specific for said analyte wherein the label is an ECL moiety, (c) a binding partner specific for said analyte linked to a magnetizable bead, (d) an ECL coreactant, and (e) an electrolyte; (2) contacting a faradaic working electrode and a capacitive counter electrode with the solution; (3) collecting the beads along the faradaic working electrode; (4) supplying electrical energy to the electrodes to cause the ECL moiety to repeatedly generate electrochemiluminescence; (5) measuring said electrochemiluminescence; and (6) determining presence or amount of said analyte from the measurement.

In some embodiments, the method can be a method for analyzing the sample for multiple analytes. For example, an array of faradaic working electrodes can be used with one or more capacitive counter electrodes wherein a measurement from one or more faradaic working electrodes is used to measure each analyte. For example, one or more faradaic working electrodes can be used with one or more capacitive counter electrodes wherein more than one analyte is measured on each faradaic working electrode.

In some embodiments, the method of generating at least one electrochemical product at a working electrode while generating a discordantly smaller amount of electrochemical byproduct at a counter electrode, comprises contacting a faradaic working electrode and a capacitive counter electrode with an electrolyte solution; and applying electrical energy between the faradaic working electrode and the capacitive counter electrode wherein the faradaic charge transferred across the faradaic working electrode is greater than the faradaic charge transferred across the capacitive counter electrode.

The discord in the amount of byproduct formed, relative to the amount of product formed, is primarily a result of the discord in faradaic charge transfer at the working and counter electrodes. In an apparatus of the present invention, and unlike traditional electrochemical apparatus, the amount of charge transferred at the faradaic working electrode is greater than the amount of charge that is transferred at the capacitive counter electrode. The difference in the amount of charge transferred at the working and counter electrodes can be, for example, greater than or equal to a factor of about 5; about 10; about 30; about 100; about 300; about 1,000; about 3,000; about 10,000, about 100,000; or more. In some embodiments the discord in faradaic charge transfer can be in the range of from about 5 to about 100,000, or from about 5 to about 10,000, or from about 5 to about 1,000, or from about 5 to about 100, or from about 10 to about 100,000, or from about 10 to about 10,000, or from about 10 to about 1,000, or from about 10 to about 100, or from about 30 to about 100,000, or from about 30 to about 10,000, or from about 30 to about 1,000, or from about 30 to about 300, or from about 100 to about 100,000, or from about 100 to about 10,000, or from about 100 to about 1,000.

In electrochemical cells known in the art, there may be a difference in the amount of byproduct formed at the counter electrode, relative to the amount of product formed at the working electrode when the half-cell reactions that occur at each of these electrodes requires a differing number of electrons. The difference between the amount of electrochemical product at the faradaic working electrode and the electrochemical byproduct at the capacitive counter electrode is determined by the stoichiometry of the redox reactions involved.

Taking into consideration the discord in faradaic charge transfer, the possibility that a different number of electrons can be required for each of the half-cell reactions, and any other processes that affect the amount of byproduct that is formed, a discordantly smaller amount of byproduct is formed at the counter electrode if the ratio of product to byproduct is greater than or equal to a factor of about 2; about 5; about 10; about 30; about 100; about 300; about 1,000; about 3,000; about 10,000, about 100,000; about 200,000 or more. For example, if the ratio of the amount of faradaic charge transferred across the working and counter electrodes is 30 and all the electrochemical reactions at the counter electrode require 1 electron while all the electrochemical reactions at the working electrode require 2 electrons, then the ratio of product to byproduct would be 15. In some embodiments, the ratio of product to byproduct can be in the range of from about 2 to about 200,000, or from about 2 to about 20,000, or from about 2 to about 2,000, or from about 2 to about 200, or from about 5 to about 200,000, or from about 5 to about 20,000, or from about 5 to about 2,000, or from about 5 to about 200, or from about 15 to about 200,000, or from about 15 to about 20,000, or from about 15 to about 2,000, or from about 15 to about 600, or from about 50 to about 200,000, or from about 50 to about 20,000, or from about 50 to about 2,000.

Coulometric methods can be used to add a small measurable amount of a species into a system, for example, into a nanosystem using an ultramicroelectrode (UME). Because of the small size of nanosystems, the usual cell separators cannot easily be employed to prevent the undesired products generated at the counter electrode from being introduced into the system. Utilizing a system with a faradaic working electrode and a capacitive counter electrode can allow both electrodes to be in contact with the electrolyte solution in a single cell, while reducing or preventing the production of undesired products.

When the polarity of the electrical energy applied to the electrodes is changed with time, current can flow alternately in both directions. For example, when the capacitive counter electrode charges to a large voltage, the polarity of the electrical energy can be reversed to discharge the capacitive counter electrode. Optionally, the counter electrode can be charged with the opposite polarity. During this switching process, the faradaic working electrode can act in turn as an anode and as a cathode (depending on the direction of current flow). While the use of two faradaic electrodes can cause both anodic and cathodic reactions to occur at the same time at differing places, this invention enables the anodic and cathodic reactions to occur at differing times at the same place. This temporal separation can be useful in several circumstances.

B. Temporal Separation Methods

Temporal separation can be useful where the counter and working electrodes are sufficiently close that reaction products from one electrode could, if generated at the same time, diffuse to and interfere with the reaction at the other electrode. For example, in-situ generation of chlorine gas from chloride ions in aqueous solution can be compromised by generation of hydroxy ions at a faradaic counter electrode by the formation of hypochlorite. Through time separation, the desired product (e.g., chlorine gas) can be used or removed (e.g., via diffusion or convection) from the electrodes before the compromising reaction occurs. The removal can be considered as a temporal-spatial separation.

In some embodiments, the temporal-spatial separation can be created by flowing liquids past the electrodes. The liquid downstream of the electrode can then comprise alternating cathodic and anodic reaction products. For example, a solution comprising dissolved oxygen gas and chloride ions can generate alternately chlorine gas and hydrogen peroxide downstream of the electrodes. This combination can be used, for example, for decontaminating a device or cartridge. In some embodiments, temporal-spatial separations can be created by reaction products differing in density (e.g., a gas and an ion). By giving the gas product time to diffuse away from the working electrode before the ion is created, the reaction products can be separated.

In some embodiments, the temporally separated reaction products are not spatially separated; rather they can be alternately used in situ. For example, the pH of a reaction cell can be alternately adjusted up and down by 1, 2, 3, 4, or more pH units by the faradaic creation of hydroxy or hydronium ions. Cycling the chemical environment in a region can have several uses. For example, a new method of DNA amplification can be made creating strand separation and renaturation cycles not by cycling temperature as is done in PCR, but by cycling the chemical environment.

C. Additional Embodiments of Apparatus and Assays Useful for Certain Methods In some embodiments, the present invention is directed to an apparatus comprising an electrochemical cell comprising: a faradaic working electrode; a capacitive counter electrode; and a container capable of receiving an electrolyte solution.

In some embodiments, the electrochemical cell at least partially encloses a sample volume.

In some embodiments, the electrochemical cell further comprises a reference electrode.

In some embodiments, the apparatus further comprises an assay-performance-substance comprising a labeled binding partner for an analyte or a labeled analog of the analyte.

In some embodiments, the apparatus further comprises a filter in fluidic connection to the faradaic working electrode and the capacitive counter electrode.

In some embodiments, the apparatus further comprises a source of electrical energy capable of being electrically connectable to the faradaic working electrode and the capacitive counter electrode.

In some embodiments, the apparatus further comprises a photodetector positioned to detect light emitted on, at or near the faradaic working electrode.

In some embodiments, the apparatus further comprises a pump arranged to be able to move liquid across or onto the faradaic working electrode.

In some embodiments, the present invention is directed to a method of for determining the presence or amount of an analyte in a sample comprising the steps of:
  (a) optionally preprocessing the sample;
  (b) contacting a faradaic working electrode to a solution comprising the optionally pre-processed sample; and an electrolyte;
  (c) contacting a capacitive counter electrode to the solution;
  (d) supplying electrical energy between the faradaic working electrode and the capacitive counter electrode sufficient to provide for faradaic charge transfer at the faradaic working electrode;
  (e) measuring at least one of (i) light, (ii) current, (iii) voltage, and (iv) charge to determine the presence or amount of the analyte in the sample.

In some embodiments, the sample is not pre-processed.

In some embodiments, the sample is pre-processed by filtering the sample with a filter, wherein the filter has a pore size rating less than or equal to about 100 microns and greater than or equal to about 10 microns In some embodiments, the sample is pre-processed by filtering the sample with a filter, wherein the filter has a pore size rating less than or equal to about 10 microns and greater than or equal to about 1 microns.

In some embodiments, the sample is pre-processed by filtering the sample with a filter, wherein the filter has a pore size rating less than or equal to about 1 micron and greater than or equal to about 0.1 microns.

In some embodiments, the sample is preprocessed by filtering the sample with a filter, wherein the filter has a pore size rating less than or equal to about 0.1 micron and greater than or equal to about 0.02 microns.

In some embodiments, the solution further comprises an assay-performance-substance comprising a labeled binding partner for an analyte or a labeled analog of the analyte.

In some embodiments, the label of the labeled binding partner for the analyte and/or the labeled analog of the analyte is the ECL moiety.

In some embodiments, the amount of analyte in the sample is determined by activating the ECL moiety in solution by applying an electrochemiluminescence-inducing electrical waveform to the faradaic working electrode; and measuring the luminescence emitted by the ECL moiety.

In some embodiments, the solution further comprises a second binding partner for the analyte wherein the second binding partner is linked to a support. In some embodiments, the support is a magnetizable bead.

In some embodiments, the method is a method for analyzing the sample for multiple analytes.

In some embodiments, the reagent that aids in the detection of the analyte or the first binding partner is an electrolyte.

In some embodiments, the first binding partner is a labeled binding partner.

In some embodiments, the labeled binding partner comprises an ECL moiety.

In some embodiments, the reagent that aids in the detection of the analyte or the first binding partner is an ECL coreactant.

In some embodiments, the first binding partner is measured by measuring the electrochemiluminescence emitted by the ECL moiety by:
  (a) inducing the ECL moiety in solution to emit light by applying an electrochemiluminescence-inducing electrical waveform to the working electrode in the presence of the ECL moiety; and
  (b) measuring the luminescence emitted by the ECL moiety.

In some embodiments, the method further comprises the step of adding to filtrate of step (b) a second binding partner for the analyte wherein the second binding partner is linked to a support. In some embodiments, the support is a magnetizable bead.

In some embodiments, the method further comprises the step of magnetically collecting the magnetizable beads along the faradaic working electrode surface through the use of a magnet.

In some embodiments, the faradaic current flow at the faradaic working electrode alternates in direction to reduce the potential across the capacitive counter electrode.

In some embodiments, the present invention is directed to a method of generating at least one electrochemical product at a working electrode while generating a discordantly smaller amount of electrochemical byproduct at a counter electrode, comprising:

contacting a faradaic working electrode with an electrolyte solution;

contacting a capacitive counter electrode with the electrolyte solution; and applying electrical energy between the faradaic working electrode and the capacitive counter electrode wherein the faradaic charge transferred across the faradaic working electrode is at least about 10 times the faradaic charge transferred across the capacitive counter electrode.

In some embodiments, the faradaic charge transferred across the faradaic working electrode is at least about 100 times the faradaic charge transferred across the capacitive counter electrode.

In some embodiments, the faradaic charge transferred across the faradaic working electrode is at least about 1,000 times the faradaic charge transferred across the capacitive counter electrode.

In some embodiments, the applied electrical energy alternates in the polarity to form at least one oxidative product and at least one reductive product at the working electrode.

In some embodiments, the faradaic working and capacitive counter electrodes are located in a flow cell and movement of the oxidative and reductive products away from the faradaic working electrode surface is facilitated by a flow of the electrolyte solution through the flow cell.

In some embodiments, the rate of alternating the polarity of the electrical energy applied to the electrodes is sufficient to allow either the oxidative product to move away from the electrode before the reductive product is formed or to allow the reductive product to move away from the electrode before the oxidative product is formed.

In some embodiments, the electrolyte solution comprises dissolved oxygen gas and chloride ions.

In some embodiments, the product of one of the oxidative half-cell reactions or the reductive half-cell reactions is a gas and the other product is an ion In some embodiments, the oxidative product comprises chlorine gas and the reductive product comprises hydrogen peroxide.

In some embodiments, the oxidative product and the reductive product are used as part of a decontamination process.

In some embodiments, the oxidative product and the reductive product is a gas and the other is an ion.

In some embodiments, the amount of the electrochemical product is increased by exposing an area of the counter electrode to the electrolyte solution that was previously unexposed to the electrolyte solution.

EXAMPLES

The following examples serve to more fully describe the manner of using the above-described invention. It is understood that these examples in no way serve to limit the true scope of this invention, but rather are presented for illustrative purposes. The following abbreviations have the following meanings. If an abbreviation is not defined within the application, the abbreviation has its generally accepted meaning.

μm=micrometers or microns
A=ampere
bpy=bipyridyl
cm=centimeter
e.g.=for example
F=farad
M=molar
min=minute
mm=millimeter
mM=millimolar
mV=millivolts
nA=nanoampere
nF=nanofarad
nm=nanometer
pA=picoampere
PMT=photomultiplier tube
s=second
TPA=tri-n-propylamine
UME=ultramicroelectrode
V=volts

Example 1

Measurement of Faradaic Current at a Working Electrode in an Electrochemical Cell having a Capacitive Counter Electrode A 25 μm diameter Pt wire (101) sealed in a glass UME (102) tip served as the faradaic electrode and contacted a few mm diameter drop of deionized (MilliQ) water placed on the $SiO_2$ film (500 nm thick) on a single crystal Si wafer (100) with a thin insulating film of $SiO_2$ functioning as the capacitive electrode. Samples of $SiO_2$/Si were prepared at SEMATECH (Austin, Tex.) by chemical vapor deposition without further treatment. In experiments where a water drop was moved along the $SiO_2$ surface under a bias as shown schematically in FIG. 1, a 2 mm diameter glass tube (103) was attached to the 25 μm Pt tip with parafilm to avoid water leakage. The tube was slightly over filled so that a water drop (104) was formed at its top to contact the $SiO_2$ surface and the drop could be moved horizontally to continuously make contact with a fresh part of the oxide surface. The total faradaic charge injected at the Pt electrode is given by $$Q_f = \int i\, dt - Q_{c,Pt} = \int i\, dt - C_{dl,Pt} A_{Pt} \Delta E = C_{dl,Si} A_{Si} \Delta E - C_{dl,Pt} A_{Pt} \Delta E \quad (1)$$

where $Q_f$ is the total faradaic charge injected, i, the total current, $Q_{c,Pt}$, the capacitive charge at the Pt electrode, $C_{dl,Pt}$, the integral capacitance of the Pt electrode, $C_{dl,Si}$ the integral capacitance of the Si electrode, $A_{Pt}$ and $A_{Si}$, the areas of Pt and Si electrodes, respectively, and $\Delta E$, the applied bias.

Once the current became negligibly small, the external circuit was disconnected for about 8 s. When it was reconnected at the same bias, the charging current was significantly smaller as shown in FIG. 2, (inset) in which the initial sharp spike was an electronic artifact resulting from capacitive coupling. When the circuit was opened for a longer time, such as 15 to 20 s, the charging current after reconnection did not appear very different than that in the inset in FIG. 2. This demonstrates that the electronic and ionic charges brought to the $SiO_2$ interface by the external potential changed only slightly at open circuit.

Example 2

Figure 3:
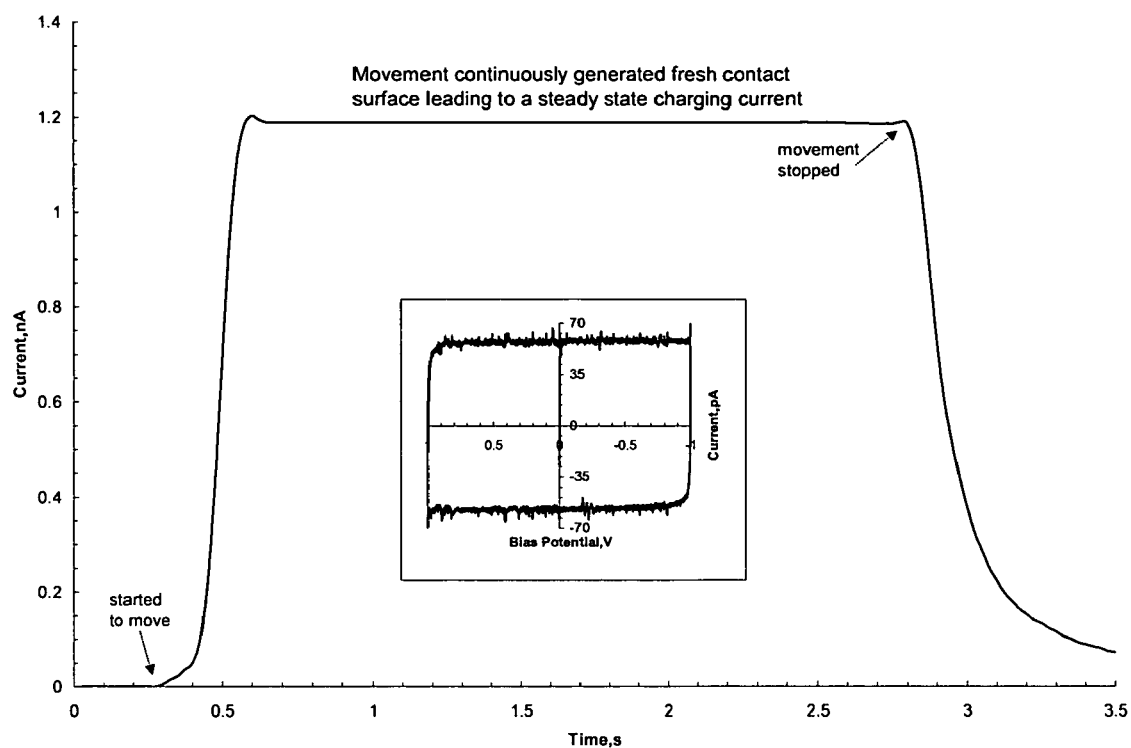
FIG. 3. Charging current recorded during the relative movement under a bias of −1 V applied between Pt and Si in a system of Pt/water/$SiO_2$/Si. Lateral scan rate, ~1 cm/s. Inset: Charging current as a function of bias with stationary tip at a scan rate of 100 mV/s.

Measurement of Faradaic Current at a Moving Working Electrode in an Electrochemical Cell having a Capacitive Counter Electrode Using the set up described in Example 1, the water drop (104) and associated Pt UME (101) were moved across the $SiO_2$ surface under a constant bias. Before movement, a bias of −1 V was applied to the tip and the surface became fully charged. Then, the tip was moved laterally by pushing the translation stage (105) manually at a rate of roughly 1 cm/s over a distance of about 0.5 to 4 cm without disconnecting the bias and the current increased as shown in FIG. 3. The current reached a steady state at the nA level, which was maintained by continuous exposure to fresh surface. The current did not drop until the movement ended and the charging at this location approached saturation (FIG. 3). The contact area of the $SiO_2$ electrode and the water drop remained essentially constant during the lateral tip movement. The steady state current depended on how fast the fresh surface was contacted. At a tip movement rate of 25 μm/s, controlled with an inchworm motor, the steady state current was about 3 pA (the leakage current was not detectable (noise floor<1 pA) with such a thick oxide layer). The 25 μm movement of the water drop in 1 s generated a new contact area corresponding to a capacitance of ~5 pF assuming a parallel capacitor with $SiO_2$ as the dielectric material. In other words, under a bias of 1 V neglecting potential drops at the Pt electrode and the solution resistance, a maximum current of ~5 pA should be obtained compared to the actual current of 3 pA actually observed. At such a low rate of tip displacement, it took several minutes for the water drop to completely move away from its previous spot. Probably the stored charge on both interfaces of $SiO_2$ (ions in solution and electronic charge in the Si) either did not move or moved too slowly to follow the water drop. The observed behavior did not depend on the polarity of the bias applied to the system. When a supporting electrolyte such as $0.1M\ Na_2SO_4$, was introduced, the system charged more quickly because of the decrease of solution resistance. However the basic features were the same.

Figure 4:
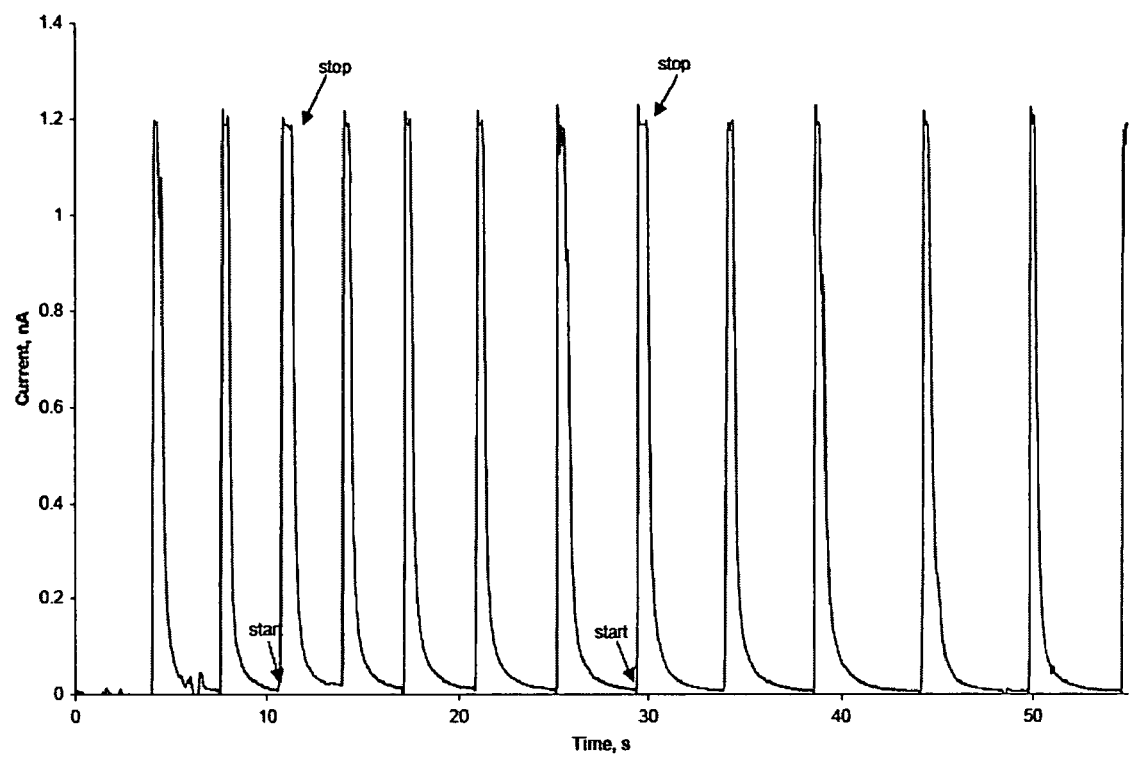
FIG. 4. Charging current, as in FIG. 3 during repeated steps, i.e., a stop-and-go lateral movement, under a constant bias of −1 V between Pt and Si. The current increased as the water drop movement started and decreased when the movement stopped, with a brief steady state charging current during the movement.

The results shown in FIG. 3 could be reproduced many times at different locations. Similar results were also obtained as the tip traveled in a stepwise, repeated stop-and-go mode as shown in FIG. 4. Each time, the charging current increased as the water drop started to move, and a steady state charging current was seen and decreased when the water drop stopped moving.

The capacitive electrode's surface of $SiO_2$ was hydrophobic (contact angle with pure water about 87° C.) and no visible trace of water was left after the drop moved away from a spot. In some cases, the water drop was moved in a pre-designed pattern so that the location of each stop could be revisited later. When the water drop was moved back to those spots, which had been previously fully charged, after a period of 10 to 20 min, no appreciable charge could be observed under the same charging conditions (the charging current was comparable to the one shown in the inset of FIG. 1), confirming that the charges remained at their original spot and did not move anywhere else. Moreover, stored charges were not discharged at a neighboring spot that was about 7.5 mm away, indicating that there was no communication among stored charges at different locations. Independent of the charging history, all of the spots could be restored to their initial state by discharging the Si under short circuit conditions. These findings agree with earlier studies of the emersion of a metal electrode from solution into high vacuum, which indicated that the solution-formed double layer still existed in the high vacuum chamber after charging of the metal electrode in solution and then transfer to vacuum under a bias. See Hansen, et al., *J. Electroanal. Chem.*, 1978, 93, 87 for further details.

A typical steady charging current was seen when the tip was stationary and the potential was scanned at a rate of 100 mV/s as shown in the inset of FIG. 3. The calculated capacitance (C=i/v, where i and v are current and scan rate, respectively) of 0.577 nF corresponding to 6.9 $nF/cm^2$ from this result fitted a value for an ideal parallel capacitor using $SiO_2$ as the dielectric material (C=∈∈$_o$A/d, where ∈ is the relative permittivity of the dielectric material, 3.9 for $SiO_2$; ∈$_o$ the permittivity of space; A the area, and d is 500 nm, the thickness of $SiO_2$) with a diameter of 3.2 mm, which closely matched the actual area contacted by the drop.

Example 3

Measurement of ECL at in an Electrochemical Cell Having a Capacitive Counter Electrode A 250 μm Pt wire was bent at a right angle, coated with epoxy cement and then polished to expose an area of about 0.02 $mm^2$ facing a photomultiplier tube (PMT, R4220p, Hamamatsu, Bridgewater, N.J.). A piece of Si with an area of ~40 $cm^2$ and coated with a ~50 nm thick $SiO_2$ film was used the counter electrode in an aqueous solution containing 0.5 mM $Ru(bpy)_3^{2+}$[tris(2,2'-bipyridine)ruthenium(II)] in 0.10 M tri-n-propylamine (TPA) with 0.10 M Tris/0.10 M $LiClO_4$ buffer (pH=8). An Autolab potentiostat (Model PGSTAT100, EcoChemie, Utrecht, The Netherlands) was used to control the applied potential with Pt as the working electrode and the Si back contact as the counter electrode. The reference electrode input on the potentiostat was connected to the counter electrode. The ECL emission and the current were recorded simultaneously during the measurement. Potential pulses from 1.4 V (30 s) to −0.5 V (20 s) were applied to the system Pt/solution/$SiO_2$/Si. In a separate measurement to obtain an ECL image, a 25 μm Pt UME tip was used with the same solution over a 9 $cm^2$ Si/$SiO_2$ surface mounted on the stage of an inverted microscope (Nikon, Model TE300, Melville, N.Y.). For additional experimental options see also Bard, A. J.; Ed., *Electrogenerated Chemiluminescence*, Marcel Dekker, New York, 2004 and Miao, et al., *J. Am. Chem. Soc.*, 2002, 124, 14478 and references therein.

Figure 5:
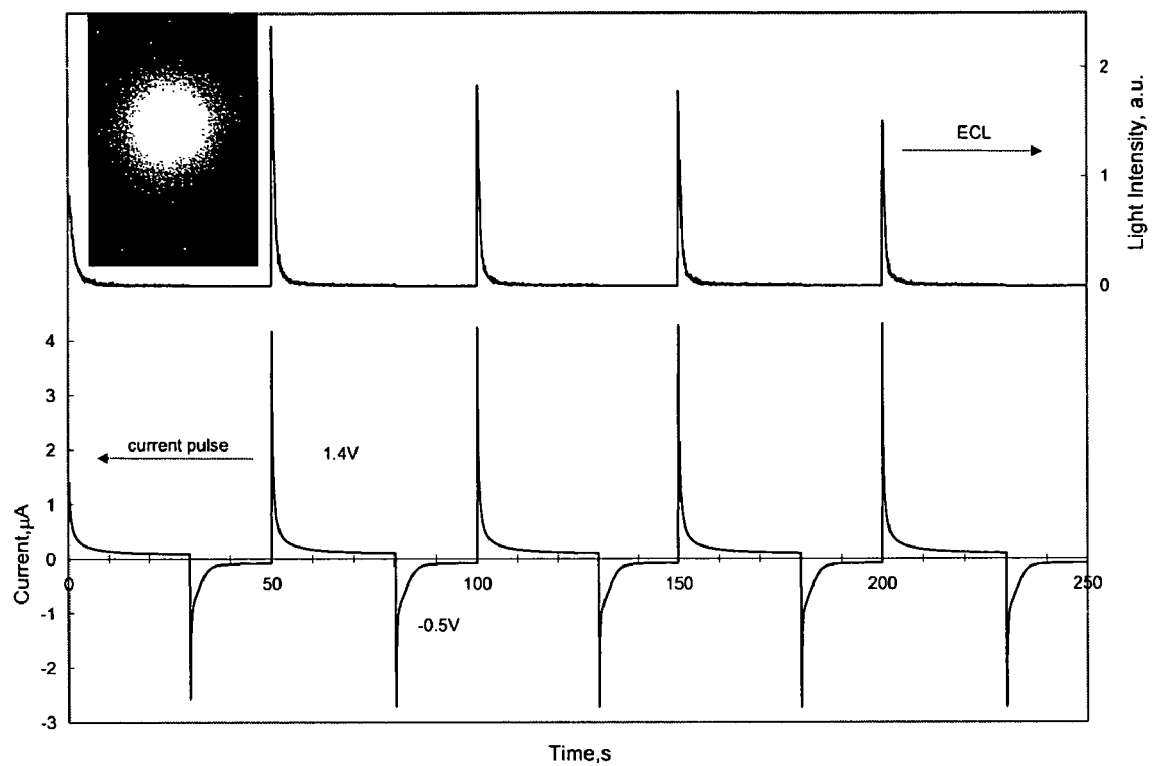
FIG. 5. Charging current (bottom) and electrogenerated chemiluminescence (top) produced in the system of Pt/water/$SiO_2$/Si with continuous applied potential pulses from 1.4 V to −0.5 V between Pt and Si, in aqueous 0.5 mM Ru(bpy)$_3^{2+}$, 0.10 M tripropylamine (TPA) and 0.10 M Tris/0.10 M LiClO$_4$ buffer (pH=8). Inset: Micrograph of an ECL image from a 25 μm Pt tip obtained with an optical microscope in a separate experiment with the same system under a bias of 1.4 V.

ECL was generated by potential steps applied between a 0.02 $mm^2$ Pt electrode and a Si/$SiO_2$ (40 $cm^2$) electrode. As shown in FIG. 5, ECL was detected immediately following the application of a potential pulse of 1.4 V to the Pt electrode, triggering a negative charging process at the $SiO_2$ interface. As the charging current decreased, the ECL emission intensity decreased. The decreasing current in this case represents charging of the counter electrode rather than the usual reactant depletion at the Pt electrode. As expected, no ECL was seen under a negative bias of −0.5 V, which served, however, to discharge the interface at the Si/$SiO_2$ electrode (with a corresponding faradaic reaction at the Pt electrode). This cycle could be repeated many times and the ECL intensity decreased slightly each time probably due to the depletion of active species near the Pt electrode surface. ECL was not detected at the blocked electrode whose leakage current was therefore negligible. In a different measurement with a 25 μm Pt tip over a 9 $cm^2$ Si/$SiO_2$ electrode with the same $Ru(bpy)_3^{2+}$/TPA solution under a constant bias of 1.4 V, an ECL image of the Pt tip was clearly seen with an inverted microscope as shown in the inset in FIG. 5. The production of ECL provides clear evidence for a faradaic process in the single electrode electrochemical system and shows that ECL can be generated in a microcell without interference from counter electrode reactions.

All references cited herein are incorporated by reference in their entirety. To the extent publications and patents or patent applications incorporated by reference contradict the disclosure contained in the specification, the specification is intended to supersede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that can vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

The foregoing description of possible implementations consistent with the present invention does not represent a comprehensive list of all such implementations or all variations of the implementations described. The description of only some implementation should not be construed as an intention to exclude other implementations. Artisans will understand how to implement the invention in the appended claims in many other ways, using equivalents and alternatives that do not depart from the scope of the following claims. Moreover, unless indicated to the contrary in the preceding description, none of the components described in the implementations is essential to the invention.

We claim:

1. An apparatus comprising an electrochemical cell comprising:
    a faradaic working electrode configured to receive an amount of current at an applied voltage;
    a first capacitive counter electrode and a second capacitive counter electrode, each having a differing capacitance;
    a photodetector positioned to detect light emitted on, at and/or near the faradaic working electrode;
    wherein the electrochemical cell is capable of receiving an electrolyte solution that can simultaneously contact the faradaic working electrode and the first capacitive counter electrode; and
    a mechanism to contact the second capacitive counter electrode to the electrolyte solution to increase the amount of current at the faradaic working electrode by application of the differing capacitance.

2. The apparatus of claim 1, wherein the capacitive counter electrode exhibits a leakage current less than or equal to about 10 μA/cm².

3. The apparatus of claim 1, wherein the capacitive counter electrode exhibits a time constant greater than or equal to about 10 seconds.

4. The apparatus of claim 1, wherein the capacitive counter electrode exhibits a time constant that is greater than or equal to about 10 times the time constant of the faradaic working electrode.

5. The apparatus of claim 1, wherein the capacitive counter electrode exhibits a leakage current less than or equal to about 1 μA/cm².

6. The apparatus of claim 1, wherein the capacitive counter electrode exhibits a time constant greater than or equal to about 100 seconds.

7. The apparatus of claim 1, wherein the capacitive counter electrode exhibits a time constant that is greater than or equal to about 100 times the time constant of the faradaic working electrode.

8. The apparatus of claim 1, wherein the faradaic working electrode comprises carbon, gold, gold alloys, platinum, platinum alloys, iridium, iridium alloys, silver, sliver alloys, nickel, nickel alloys, stainless steel, or mercury.

9. The apparatus of claim 1, wherein the capacitive counter electrode comprises a material whose bulk resistivity is less than or equal to about $10^{-2}$ Ωm at 20° C., covered by an electrically insulating material having a bulk resistivity greater than or equal to about $10^{-4}$ Ωm at 20° C. wherein the insulating material has a mean thickness that is less than or equal to about 1 μm.

10. An apparatus comprising an electrochemical cell comprising:
    a faradaic working electrode configured to receive an amount of current at an applied voltage;
    a first capacitive counter electrode and a second capacitive counter electrode, each having differing capacitance;
    a reversibly movable magnet for collecting magnetizable beads at the surface of the faradaic working electrode; and
    a photodetector positioned to detect light emitted on, at and/or near the faradaic working electrode;
    wherein the electrochemical cell is capable of receiving an electrolyte solution that can simultaneously contact the faradaic working electrode and the first capacitive counter electrode; and
    a mechanism to contact the second capacitive counter electrode to the electrolyte solution to increase the amount of current at the faradaic working electrode by application of the differing capacitance.

11. The apparatus of claim 10, wherein the reversibly movable magnet is reversibly movable to and from a position disposed substantially beneath the faradaic working electrode.

12. The apparatus of claim 10, further comprising an assay-performance-substance comprising an ECL moiety and a labeled binding partner for an analyte or a labeled analog of the analyte.

13. The apparatus of claim 12, further comprising a vapor barrier substantially enclosing the assay-performance-substance.

14. An apparatus comprising an electrochemical cell comprising:
    a faradaic working electrode configured to receive an amount of current at an applied voltage;
    a first capacitive counter electrode and a second capacitive counter electrode, each having a differing capacitance;
    wherein the electrochemical cell is capable of receiving an electrolyte solution that can simultaneously contact the faradaic working electrode and the first capacitive counter electrode; and
    a mechanism to contact the second capacitive counter electrode to the electrolyte solution to increase the amount of current at the faradaic working electrode by application of the differing capacitance.

15. The apparatus of claim 14, further comprising an assay-performance-substance comprising an ECL moiety and a labeled binding partner for an analyte or a labeled analog of the analyte.

16. The apparatus of claim 15, further comprising a vapor barrier substantially enclosing the assay-performance-substance.

17. The apparatus of claim 14, further comprising a reversibly movable magnet that is reversibly movable to and from a position disposed substantially beneath the faradaic working electrode.

* * * * *